(12) United States Patent
Prior et al.

(10) Patent No.: US 9,681,868 B2
(45) Date of Patent: Jun. 20, 2017

(54) DEVICES, SYSTEMS, AND METHODS FOR WOUND CLOSURE

(71) Applicant: COVIDIEN LP, Mansfield, MA (US)

(72) Inventors: Scott J. Prior, Shelton, CT (US); Jaroslaw T. Malkowski, Trumbull, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 138 days.

(21) Appl. No.: 14/337,391

(22) Filed: Jul. 22, 2014

(65) Prior Publication Data
US 2015/0038800 A1 Feb. 5, 2015

Related U.S. Application Data

(60) Provisional application No. 61/861,732, filed on Aug. 2, 2013, provisional application No. 61/882,742, filed on (Continued)

(51) Int. Cl.
*A61B 17/04* (2006.01)
*A61B 17/06* (2006.01)
*A61B 17/00* (2006.01)

(52) U.S. Cl.
CPC .... *A61B 17/06166* (2013.01); *A61B 17/0057* (2013.01); *A61B 17/0482* (2013.01);
(Continued)

(58) Field of Classification Search
CPC . A61B 17/0057; A61B 17/04; A61B 17/0482; A61B 2017/00349
(Continued)

(56) References Cited

U.S. PATENT DOCUMENTS 5,499,997 A 3/1996 Sharpe et al.
5,507,757 A 4/1996 Sauer et al.
(Continued)

FOREIGN PATENT DOCUMENTS

EP 2412317 A1 2/2012
WO 95/02998 A1 2/1995
(Continued)

OTHER PUBLICATIONS

International Search Report corresponding to counterpart Int'l Appln. No. PCT/US2014/048919 mailed Nov. 7, 2014.
(Continued)

*Primary Examiner* — Nicolas Plionis

(57) ABSTRACT

A wound closure system includes a device, a sleeve, and a needle assembly. The device includes a shaft and one or more arms movable relative to the shaft between a retracted position and a deployed position. The sleeve is removably positionable about the shaft and is slidable about the shaft to retain tissue between the distal end of the sleeve and the arms when the arms are in the deployed position. The needle assembly includes a base one or more needles insertable through respective needle lumens of the sleeve. The base defines a central aperture for removably positioning the base about the shaft. The base is slidable relative to the shaft and sleeve between a proximal position, wherein the needles are disposed within respective needle lumens, and a distal position, wherein the needles extend from respective needle lumens towards respective arms.

14 Claims, 29 Drawing Sheets

Related U.S. Application Data on Sep. 26, 2013, provisional application No. 61/882,745, filed on Sep. 26, 2013, provisional application No. 61/882,750, filed on Sep. 26, 2013, provisional application No. 61/882,754, filed on Sep. 26, 2013, provisional application No. 61/882,758, filed on Sep. 26, 2013, provisional application No. 61/882,759, filed on Sep. 26, 2013.

(52) U.S. Cl.
CPC .......... *A61B 17/06004* (2013.01); *A61B 2017/00623* (2013.01); *A61B 2017/00637* (2013.01); *A61B 2017/00663* (2013.01); *A61B 2017/0472* (2013.01); *A61B 2017/06009* (2013.01)

(58) Field of Classification Search
USPC ........................................ 606/103, 139, 144
See application file for complete search history.

(56) References Cited

U.S. PATENT DOCUMENTS

| | | | |
|---|---|---|---|
| 5,527,343 A | 6/1996 | Bonutti | |
| 5,653,716 A | 8/1997 | Malo et al. | |
| 5,716,369 A | 2/1998 | Riza | |
| 5,817,111 A | 10/1998 | Riza | |
| 5,846,253 A | 12/1998 | Buelna et al. | |
| 5,860,991 A | 1/1999 | Klein et al. | |
| 5,868,762 A | 2/1999 | Cragg et al. | |
| 5,899,911 A | 5/1999 | Carter | |
| 5,902,311 A | 5/1999 | Andreas et al. | |
| 5,948,001 A | 9/1999 | Larsen | |
| 5,972,005 A | 10/1999 | Stalker et al. | |
| 5,993,467 A * | 11/1999 | Yoon ................. | A61B 17/0469 606/147 |
| 5,993,474 A | 11/1999 | Ouchi | |
| 6,022,360 A | 2/2000 | Reimels et al. | |
| 6,036,699 A | 3/2000 | Andreas et al. | |
| 6,059,800 A | 5/2000 | Hart et al. | |
| 6,099,550 A | 8/2000 | Yoon | |
| 6,110,184 A | 8/2000 | Weadock | |
| 6,136,010 A | 10/2000 | Modesitt et al. | |
| 6,245,079 B1 | 6/2001 | Nobles et al. | |
| 6,245,080 B1 | 6/2001 | Levinson | |
| 6,296,648 B1 | 10/2001 | Boche et al. | |
| 6,315,753 B1 * | 11/2001 | Cragg ................. | A61B 17/0057 604/15 |
| 6,355,050 B1 | 3/2002 | Andreas et al. | |
| 6,398,796 B2 | 6/2002 | Levinson | |
| 6,491,707 B2 | 12/2002 | Makower et al. | |
| 6,500,184 B1 | 12/2002 | Chan et al. | |
| 6,517,553 B2 | 2/2003 | Klein et al. | |
| 6,551,331 B2 | 4/2003 | Nobles et al. | |
| 6,743,241 B2 | 6/2004 | Kerr | |
| 6,770,084 B1 | 8/2004 | Bain et al. | |
| 6,896,685 B1 | 5/2005 | Davenport | |
| 6,939,357 B2 | 9/2005 | Navarro et al. | |
| 7,004,952 B2 | 2/2006 | Nobles et al. | |
| 7,048,749 B2 | 5/2006 | Kortenbach et al. | |
| 7,090,686 B2 | 8/2006 | Nobles et al. | |
| 7,291,155 B2 | 11/2007 | Batke et al. | |
| 7,449,024 B2 | 11/2008 | Stafford | |
| 7,462,188 B2 | 12/2008 | McIntosh | |
| 7,601,161 B1 | 10/2009 | Nobles et al. | |
| 7,722,629 B2 | 5/2010 | Chambers | |
| 7,736,388 B2 | 6/2010 | Goldfarb et al. | |
| 7,824,419 B2 | 11/2010 | Boraiah | |
| 7,850,701 B2 | 12/2010 | Modesitt et al. | |
| 8,038,687 B2 | 10/2011 | Pipenhagen et al. | |
| 8,172,860 B2 | 5/2012 | Zung et al. | |
| 8,211,122 B2 | 7/2012 | McIntosh | |
| 8,317,679 B2 | 11/2012 | Surti | |
| 8,348,962 B2 | 1/2013 | Nobles et al. | |
| 2002/0016614 A1 | 2/2002 | Klein et al. | |
| 2002/0049453 A1 | 4/2002 | Nobles et al. | |
| 2003/0009180 A1 | 1/2003 | Hinchliffe et al. | |
| 2003/0028201 A1 | 2/2003 | Navarro et al. | |
| 2004/0092964 A1 | 5/2004 | Modesitt et al. | |
| 2004/0098047 A1 | 5/2004 | Frazier et al. | |
| 2004/0186487 A1 | 9/2004 | Klein et al. | |
| 2004/0199185 A1 | 10/2004 | Davignon | |
| 2004/0225301 A1 | 11/2004 | Roop et al. | |
| 2004/0249412 A1 * | 12/2004 | Snow ................. | A61B 17/0057 606/213 |
| 2005/0119670 A1 | 6/2005 | Kerr | |
| 2005/0212221 A1 | 9/2005 | Smith et al. | |
| 2006/0020274 A1 * | 1/2006 | Ewers ................. | A61B 17/0469 606/148 |
| 2006/0195120 A1 | 8/2006 | Nobles et al. | |
| 2007/0055379 A1 * | 3/2007 | Stone ................. | A61B 17/0057 623/17.16 |
| 2007/0203507 A1 | 8/2007 | McLaughlin et al. | |
| 2007/0250112 A1 | 10/2007 | Ravikumar et al. | |
| 2008/0033459 A1 | 2/2008 | Shafi et al. | |
| 2008/0097480 A1 | 4/2008 | Schorr et al. | |
| 2008/0097481 A1 | 4/2008 | Schorr et al. | |
| 2008/0255592 A1 | 10/2008 | Hsu et al. | |
| 2010/0012152 A1 | 1/2010 | Hansen | |
| 2010/0145364 A1 * | 6/2010 | Keren ................. | A61B 17/0469 606/144 |
| 2010/0262166 A1 | 10/2010 | Boraiah et al. | |
| 2011/0082475 A1 | 4/2011 | Smith | |
| 2011/0144448 A1 * | 6/2011 | Shelton, IV ....... | A61B 17/3423 600/216 |
| 2011/0237901 A1 | 9/2011 | Duke et al. | |
| 2011/0270282 A1 | 11/2011 | Lemke | |
| 2011/0313433 A1 | 12/2011 | Woodard, Jr. et al. | |
| 2012/0010634 A1 | 1/2012 | Crabb et al. | |
| 2012/0029532 A1 | 2/2012 | Hodgkinson et al. | |
| 2012/0143221 A1 | 6/2012 | Weisel et al. | |
| 2012/0191109 A1 | 7/2012 | Rockrohr | |
| 2012/0245603 A1 * | 9/2012 | Voss ................. | A61B 17/0057 606/151 |
| 2013/0079597 A1 | 3/2013 | Auerbach et al. | |
| 2013/0165956 A1 | 6/2013 | Sherts et al. | |

FOREIGN PATENT DOCUMENTS

| | | |
|---|---|---|
| WO | 2011/128392 A1 | 10/2011 |
| WO | 2012/093094 A1 | 7/2012 |
| WO | 2013/105993 A2 | 7/2013 |

OTHER PUBLICATIONS

International Search Report corresponding to counterpart Int'l Appln. No. PCT/US2014/048907 mailed Nov. 12, 2014.
International Search Report and Written Opinion corresponding to counterpart Int'l Appln. No. PCT/US2014/048892 dated Nov. 25, 2014.
Extended European Search Report corresponding to counterpart Int'l Appln. No. EP 14 83 1785.2 dated Mar. 17, 2017.
Extended European Search Report corresponding to counterpart Int'l Appln. No. EP 14832198.7 dated Apr. 18, 2017.

\* cited by examiner

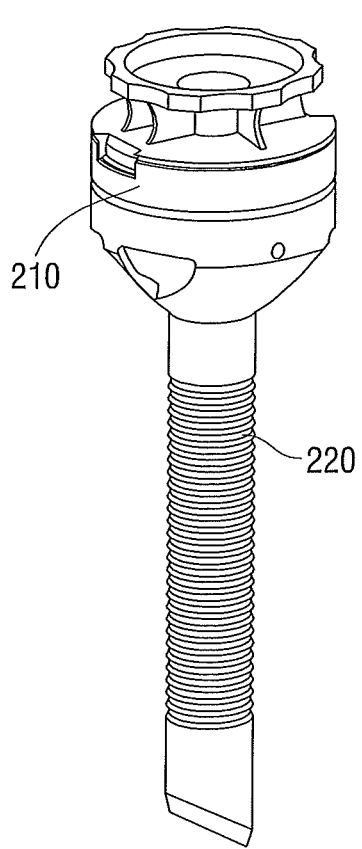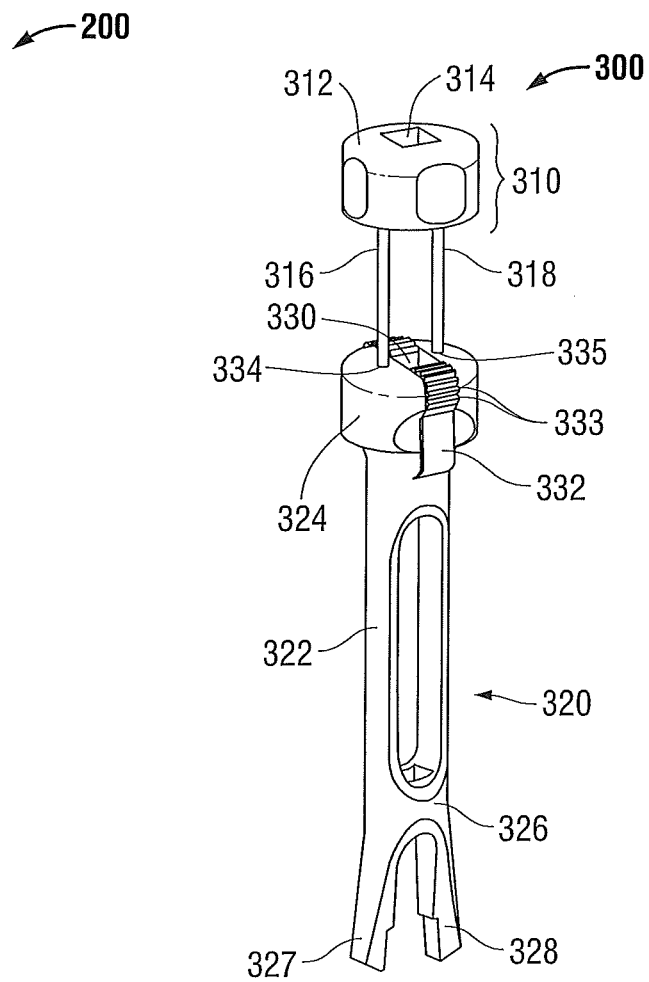
FIG. 3
FIG. 4

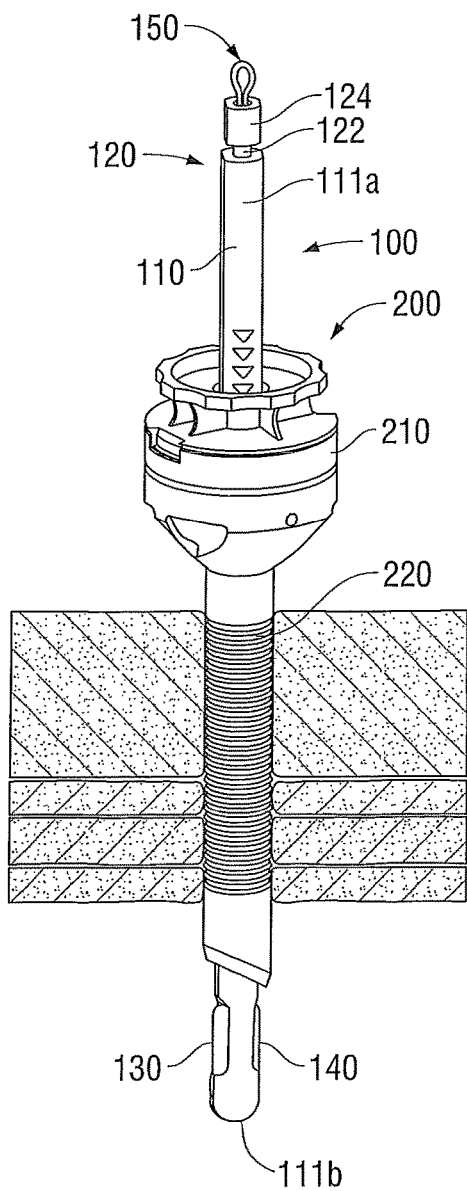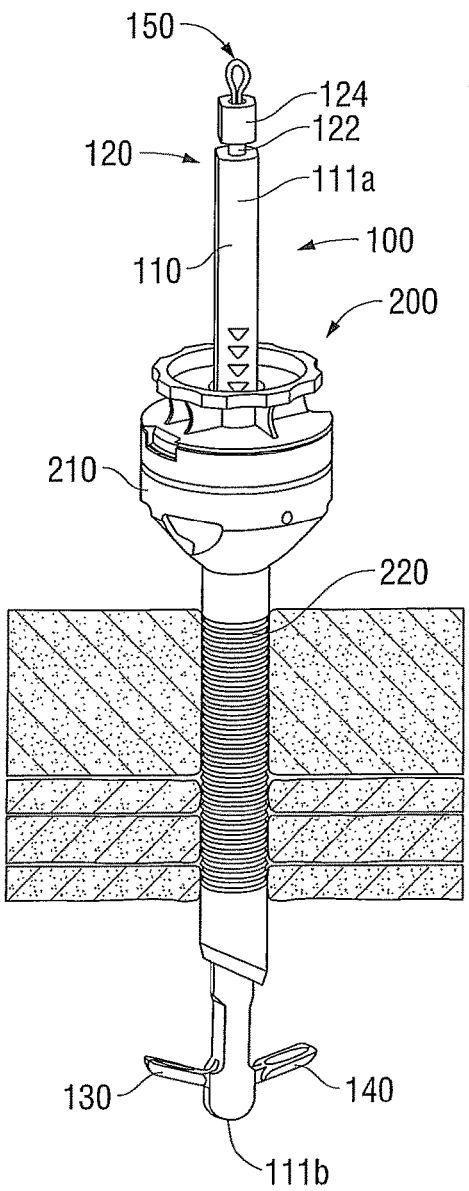
FIG. 5A  FIG. 5B

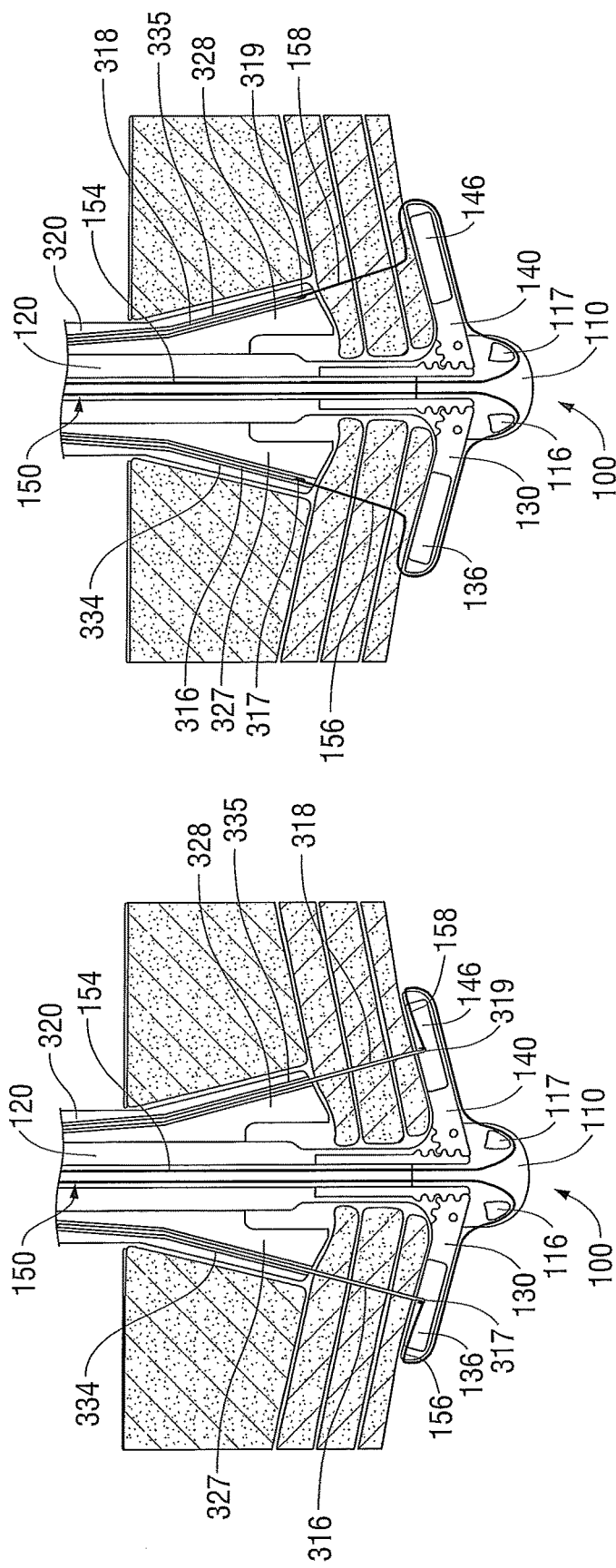

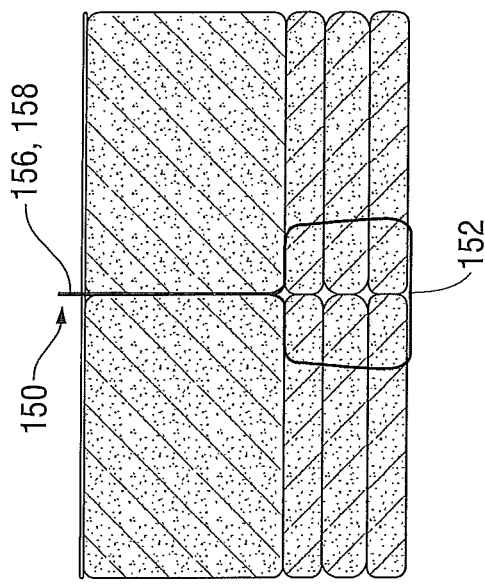
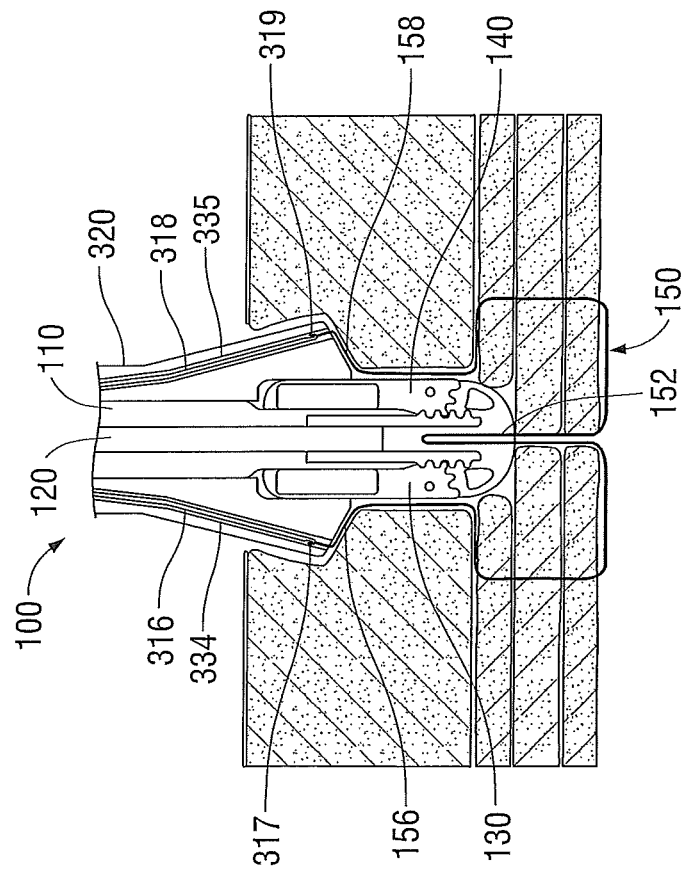

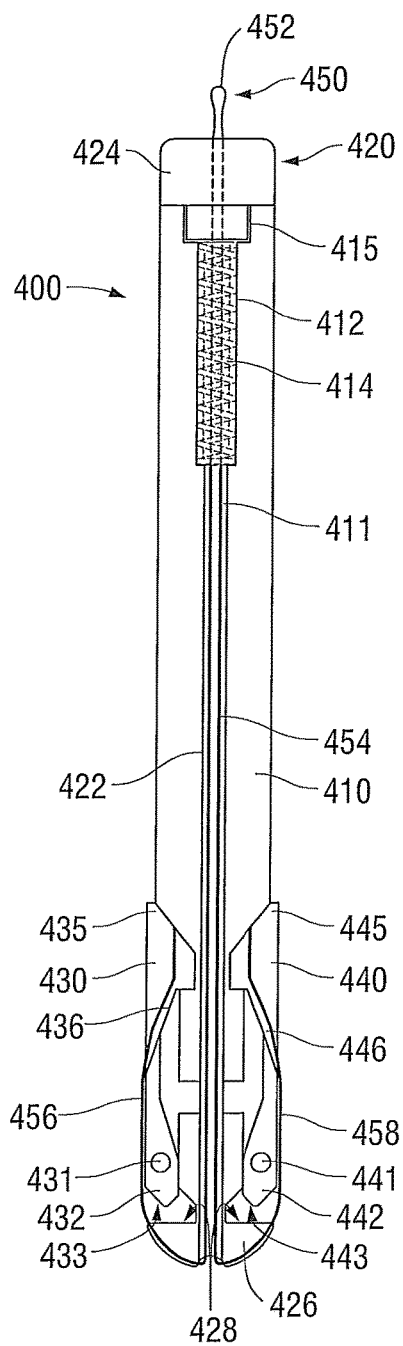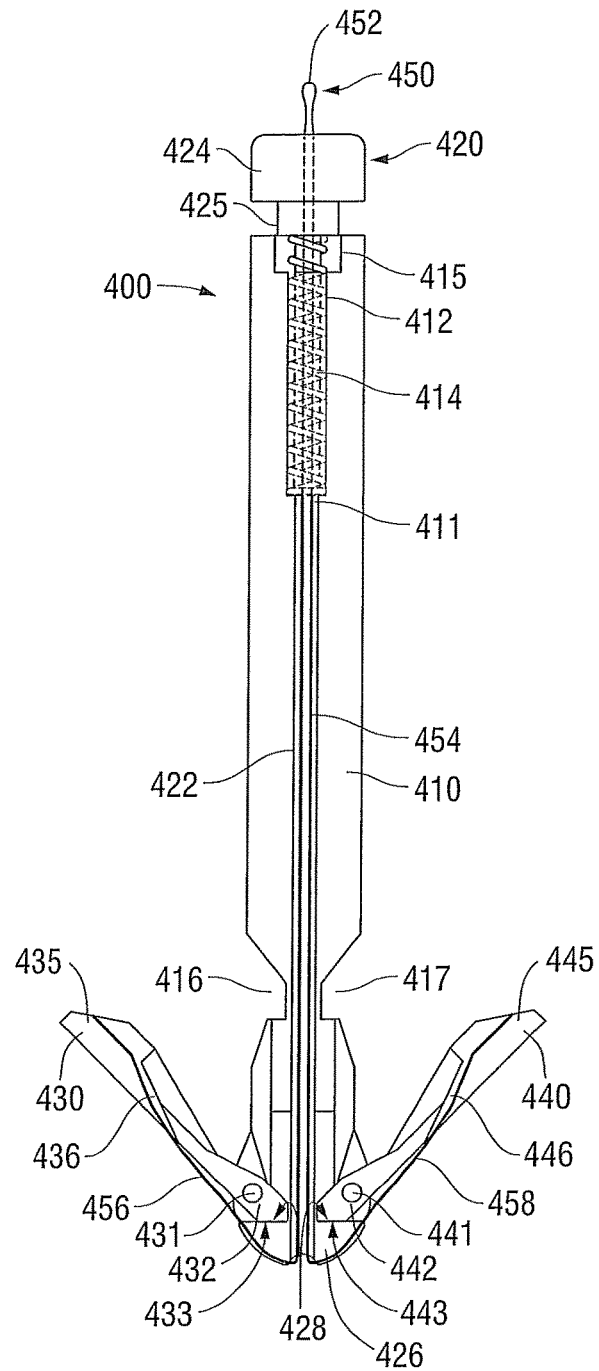
FIG. 10A
FIG. 10B

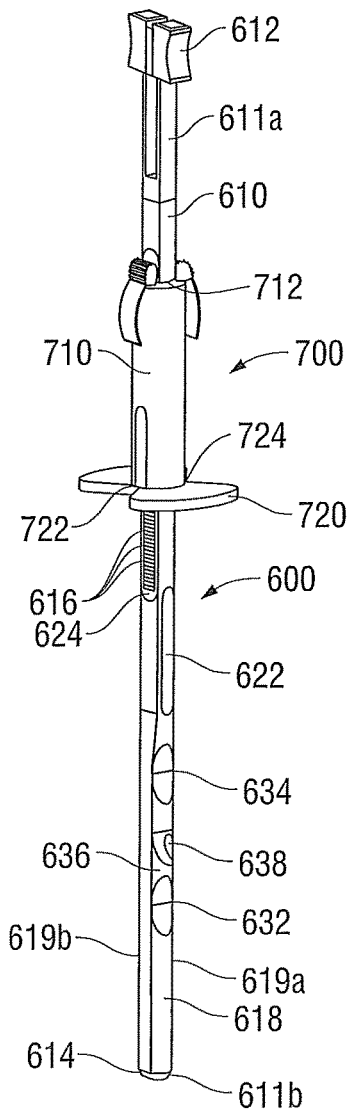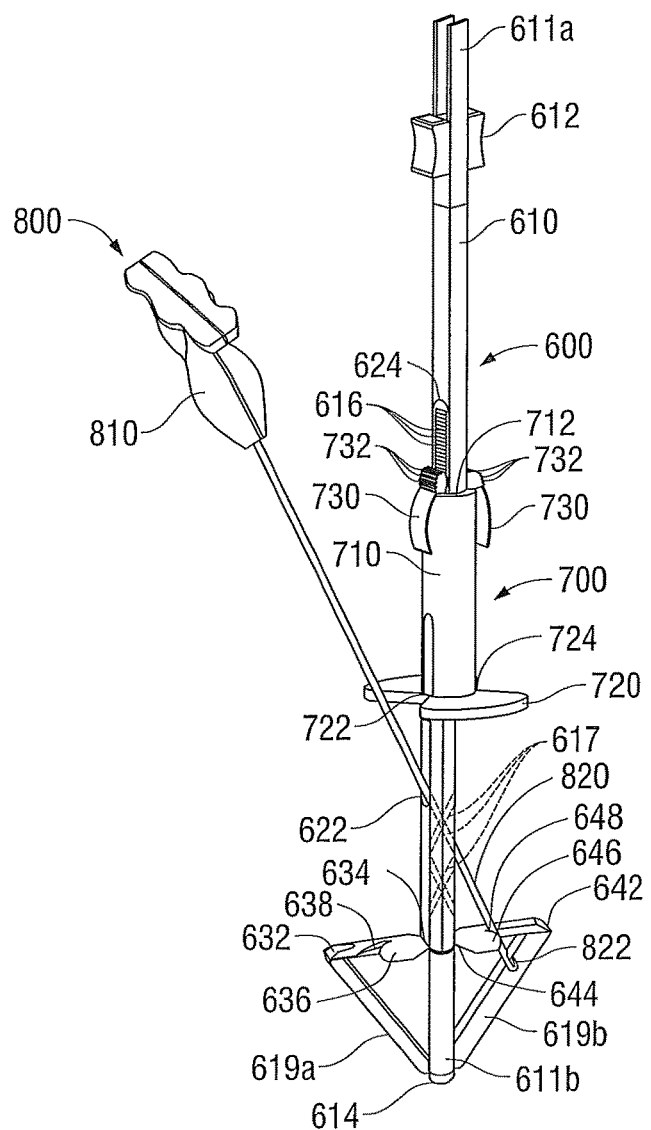
FIG. 15A
FIG. 15B

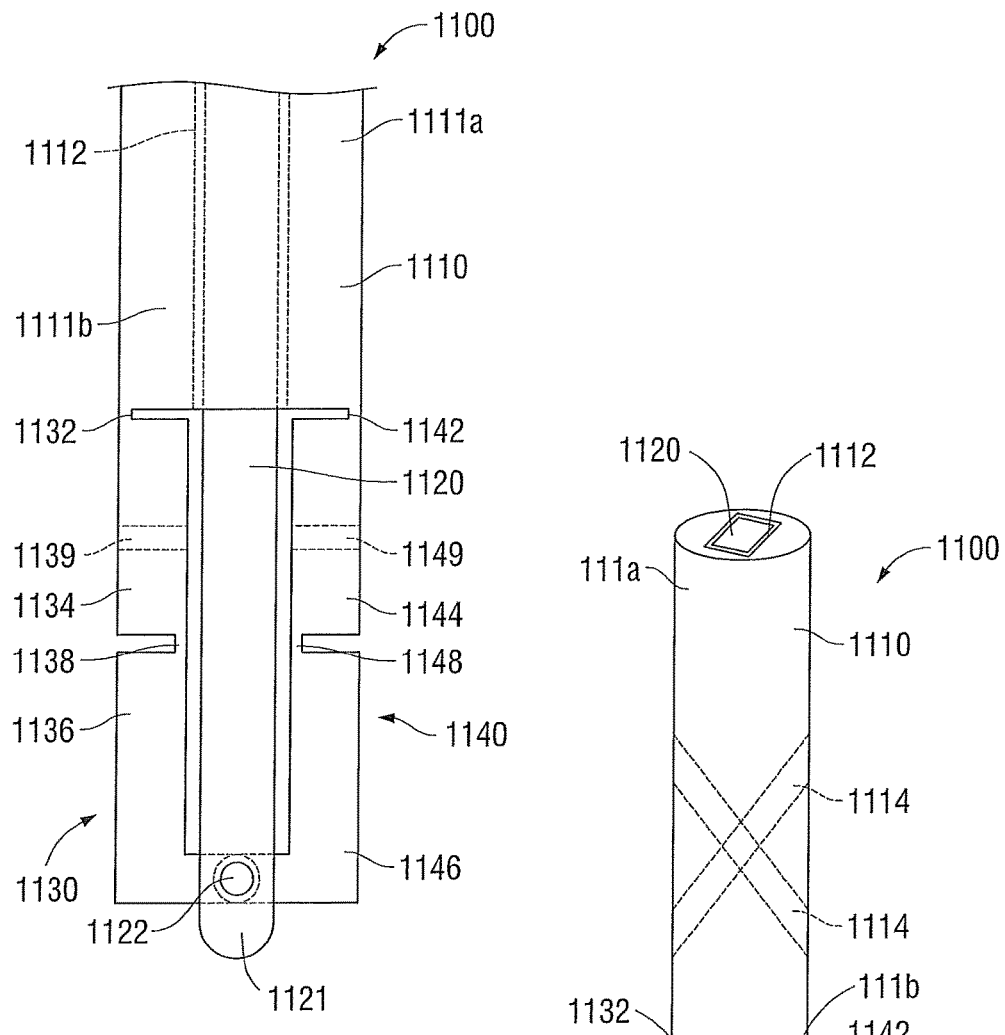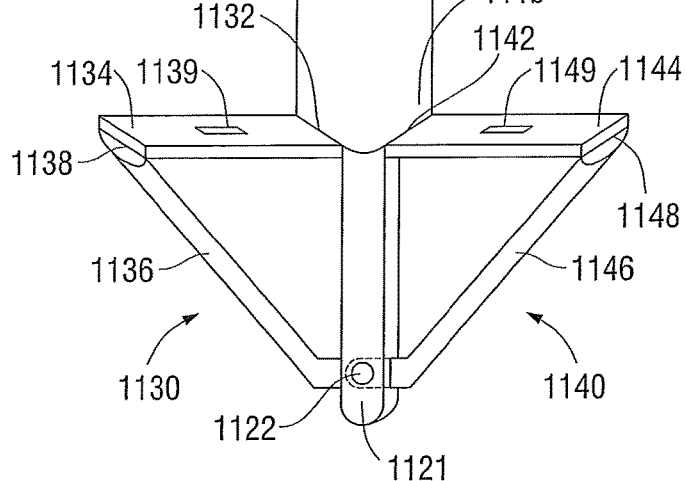

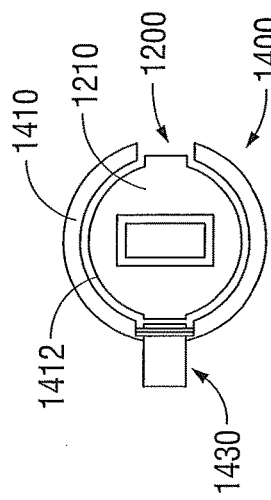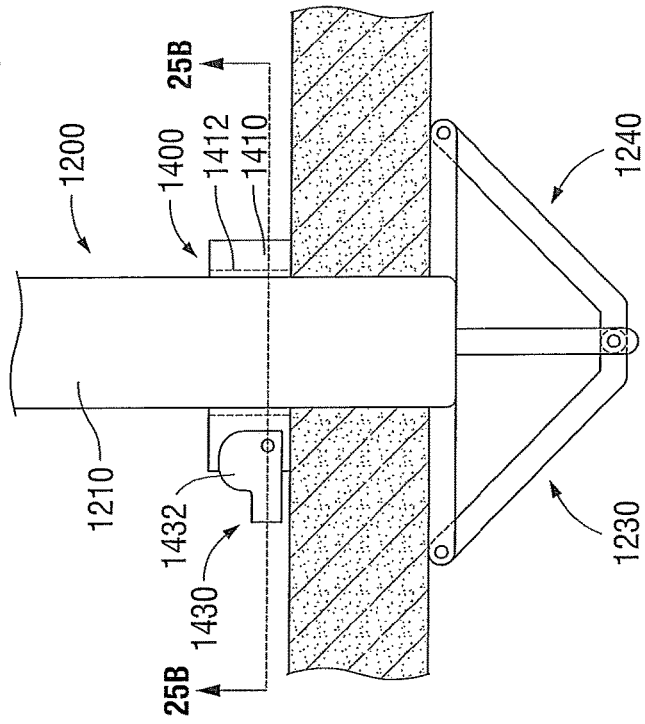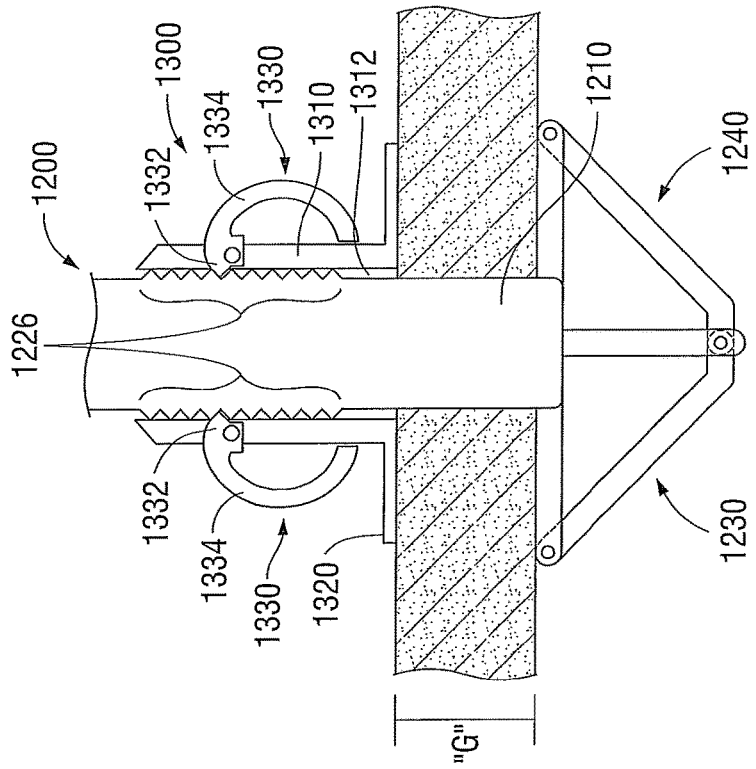

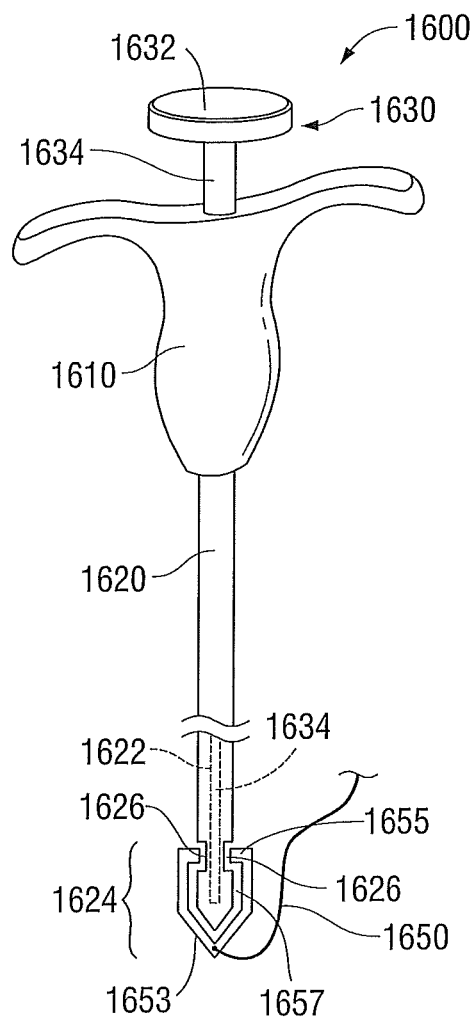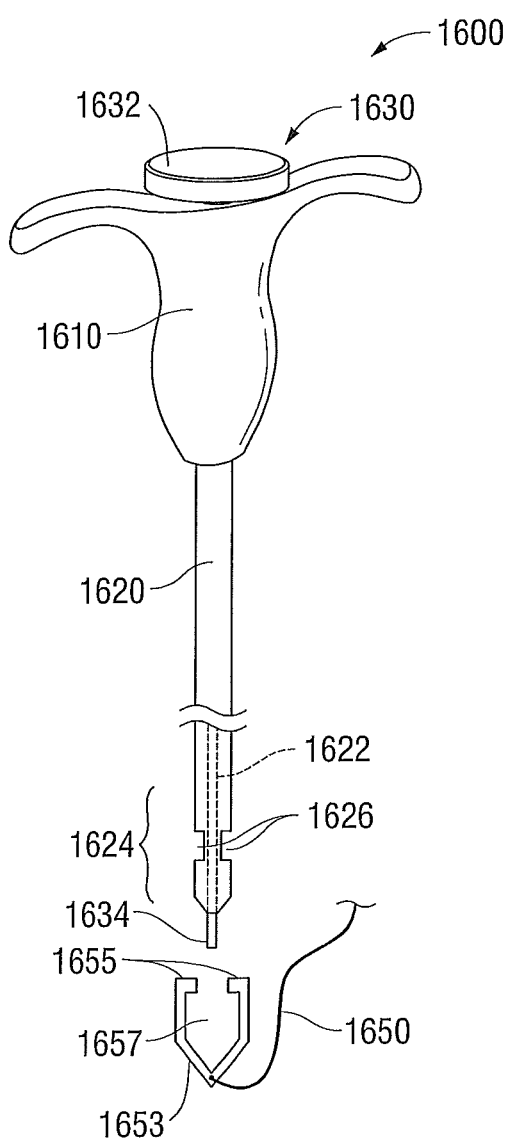
FIG. 29A
FIG. 29B

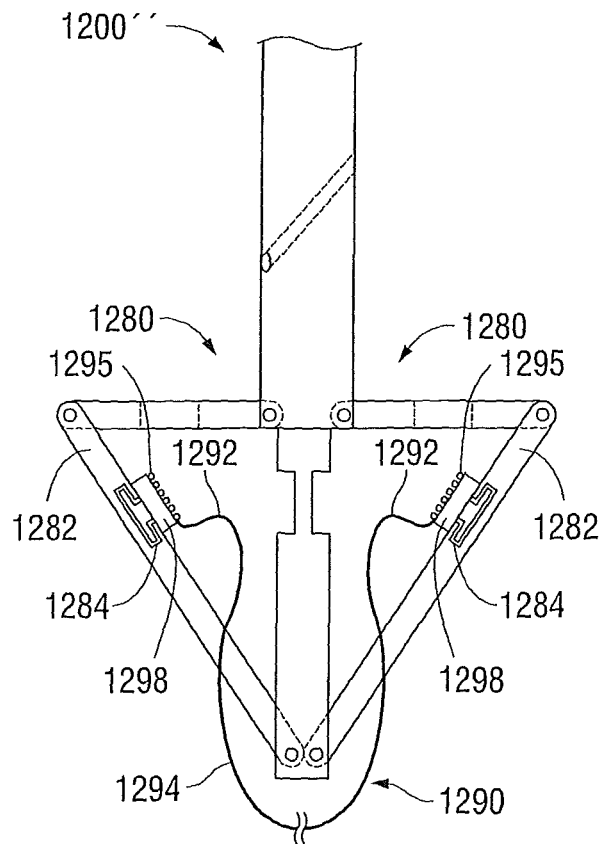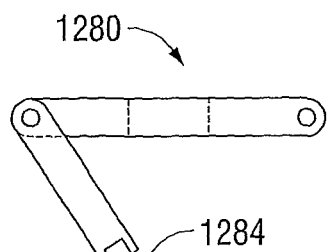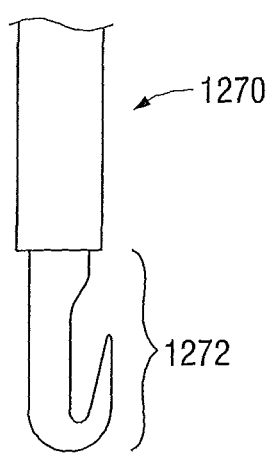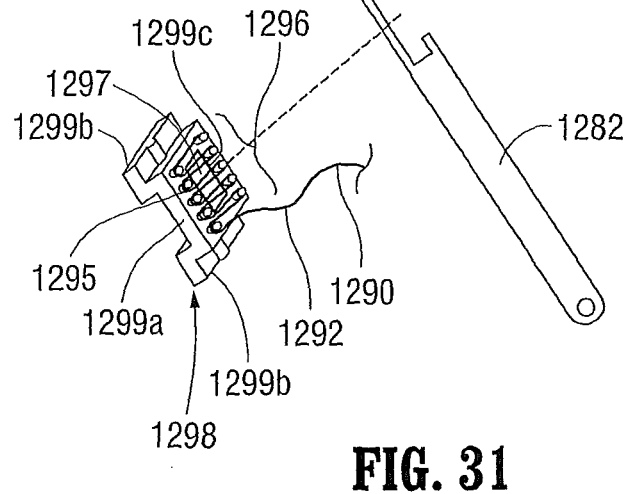
FIG. 30
FIG. 31
FIG. 32

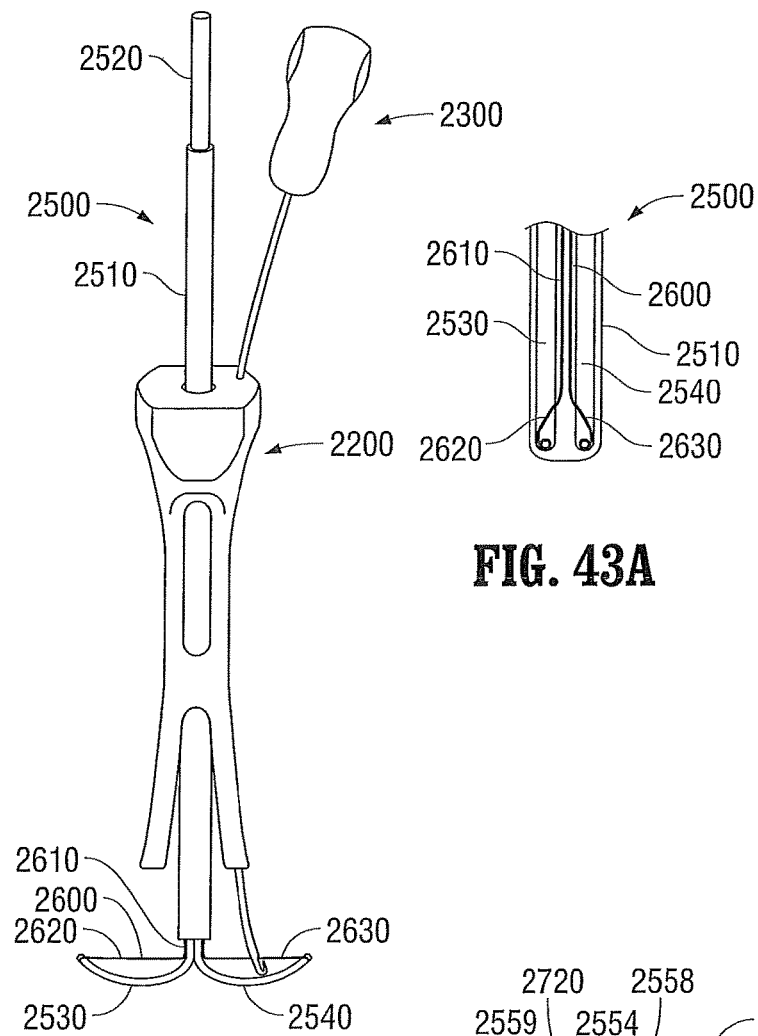
FIG. 42
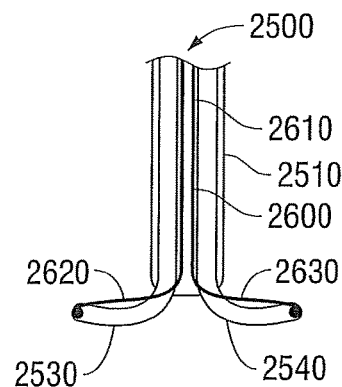
FIG. 43A
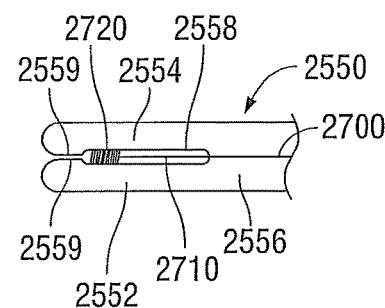
FIG. 43B
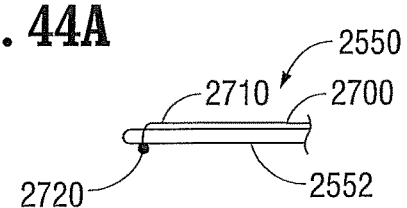
FIG. 44A
FIG. 44B

DEVICES, SYSTEMS, AND METHODS FOR WOUND CLOSURE

CROSS-REFERENCE TO RELATED APPLICATIONS

This application claims the benefit of, and priority to, U.S. Provisional Patent Application No. 61/861,732, filed on Aug. 2, 2013; U.S. Provisional Patent Application No. 61/882,742, filed on Sep. 26, 2013; U.S. Provisional Patent Application No. 61/882,745, filed on Sep. 26, 2013; U.S. Provisional Patent Application No. 61/882,750, filed on Sep. 26, 2013; U.S. Provisional Patent Application No. 61/882,754, filed on Sep. 26, 2013; U.S. Provisional Patent Application No. 61/882,758, filed on Sep. 26, 2013; and U.S. Provisional Patent Application No. 61/882,759, filed on Sep. 26, 2013.

This application is related to U.S. patent application Ser. No. 14/337,465, filed on Jul. 22, 2014; U.S. patent application Ser. No. 14/337,322, filed on Jul. 22, 2014; U.S. patent application Ser. No. 14/337,415, filed on Jul. 22, 2014; U.S. patent application Ser. No. 14/337,491, filed on Jul. 22, 2014; and U.S. patent application Ser. No. 14/337,800, filed on Jul. 22, 2014.

The entire contents of each of the above applications are hereby incorporated herein by reference.

BACKGROUND

Technical Field

The present disclosure relates to wound closure and, more particularly, to devices, systems, and methods for closing a wound or opening in tissue.

Background of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide access by way of a cannula through the abdominal wall. Generally, a trocar and/or cannula is placed through the abdominal wall for introduction of surgical instrumentation which is necessary to carry out the surgical procedure. In this manner, the surgeon may introduce a surgical instrument such as a forceps, scissors, clip applier, stapler or any other surgical instrument as desired during the particular surgical procedure. Once the procedure is complete, it is necessary to close the wound or opening.

SUMMARY

In accordance with the present disclosure, a wound closure system is provided including a wound closure device, a sleeve, and a needle assembly. The wound closure device is configured for insertion into an opening in tissue and includes an elongated shaft and one or more arms coupled to the elongated shaft in a distal region of the elongated shaft. Each arm is movable relative to the shaft between a retracted position and a deployed position, wherein each arm extends outwardly from the shaft. The sleeve defines a proximal end, a distal end, a central passage extending longitudinally through the sleeve, and one or more needle lumens extending longitudinally through the sleeve. The central passage is configured to receive the shaft for removably positioning the sleeve about the shaft. The sleeve is slidable about the shaft to retain tissue between the distal end of the sleeve and each arm when the arm(s) is disposed in the deployed position.

The needle assembly includes a base member and one or more needles extending distally from the base member. Each needle is slidably insertable through one of the needle lumens. The base member defines a central aperture configured to receive the shaft for removably positioning the base member about the shaft. The base member is slidable about the shaft and relative to the sleeve between a proximal position, wherein each needle is disposed within a respective needle lumen, and a distal position, wherein each needle extends from its respective needle lumen towards a respective arm.

In embodiments, the wound closure device further includes a plunger slidably disposed within a central bore of the shaft. The plunger is coupled to arm(s) in a distal region of the plunger and is selectively translatable relative to the shaft between a first position and a second position for moving the arm(s) between the retracted position and the deployed position.

In embodiments, each arm is pivotably coupled to the shaft and has a pinion member. The plunger has one or more gear racks, each disposed in meshed engagement with one of the pinion members such that translation of the plunger relative to the shaft pivots each arm between the retracted position and the deployed position.

In embodiments, each arm is pivotably coupled to the shaft and defines a first cam surface. The plunger defines a second cam surface such that translation of the plunger relative to the shaft urges the second cam surface into contact with each first cam surface to transition each arm from the retracted position to the deployed position.

In embodiments, each arm is biased towards the retracted position.

In embodiments, each arm defines a suture-retaining void. In the distal position, each needle extends from its respective needle lumen into the suture-retaining void of the respective arm.

In embodiments, the sleeve includes one or more fingers. Each finger is aligned with an arm when the arm is in the deployed position. One of the needle lumens extends through each of the fingers.

In embodiments, the shaft includes a plurality of first ratchet components disposed on an outer surface of the shaft and the sleeve includes at least one second ratchet component extending into the central passage. The first and second ratchet components are engagable with one another to retain the sleeve in a position relative to the shaft.

In embodiments, the system further includes a surgical access device configured for positioning within an opening in tissue. The shaft is insertable through the surgical access device and the surgical access device is proximally movable about the shaft.

In embodiments, the system further includes a suture with a first portion extending distally from the shaft, a second portion extending from the first portion distally through the shaft, and a third portion extending from the second portion to the arm(s). The third portion is releasably retained via the one or more of the arms.

In embodiments, a distal end of each needle is configured to retrieve the third portion of the suture when in the distal position.

Another wound closure system provided in accordance with the present disclosure includes a wound closure device, a sleeve, and a needle assembly. The wound closure device includes an elongated shaft defining a longitudinal passageway extending therethrough and a plunger slidably disposed within the elongated shaft. The plunger defines a pair of spring arms extending distally therefrom. Each spring arm is configured to retain a portion of a suture and is biased towards a spread position wherein the spring arms extend radially outwardly from the plunger and relative to one another. The plunger is slidable relative to the shaft between a retracted position, wherein the spring arms are disposed within the longitudinal passageway in a contracted position, and an extended position, wherein the spring arms extend from the elongated shaft in the spread position. The sleeve defines a proximal end, a distal end, a central passage extending longitudinally through the sleeve, and at least one curved needle lumen extending longitudinally through the sleeve. The central passage is configured to receive the shaft for removably positioning the sleeve about the shaft. The sleeve is slidable about the shaft to retain tissue between the distal end of the sleeve and the spring arms when the spring arms are disposed in the spread position. The needle assembly includes a base member and a needle extending distally from the base member. The needle is slidably insertable through one of the curved needle lumens such that the curved needle lumen directs the needle toward a spring atm for retrieving the portion of suture therefrom.

In embodiments, each spring arm defines a pair of fingers at a free end thereof. The fingers define an opening therebetween that is configured to receive the portion of suture therethrough.

In embodiments, each needle defines a hooked distal end.

A method of closing an opening in tissue is also provided in accordance with the present disclosure. The method includes positioning a surgical access device within an opening in tissue and inserting a wound closure device through the surgical access device and into an internal surgical site, e.g., any of the wound closure devices detailed above or other suitable wound closure device. The method further includes moving the first arm of the wound closure device from a retracted position to a deployed position such that the first arm extends outwardly from the shaft within the internal surgical site. The method further includes withdrawing the surgical access device from the opening in tissue by moving it proximally about the wound closure device. The method further includes sliding a sleeve about the shaft to retain tissue between the distal end of the sleeve and the first arm. The method further includes advancing a first needle through the sleeve, tissue adjacent the opening in tissue, and into the first arm, retrieving the first portion of the suture retained by the first arm with the first needle, and withdrawing the first needle and the first portion of the suture proximally from the first arm and through tissue adjacent the opening in tissue.

In embodiments, the wound closure device includes a second arm. In such embodiments, the method further includes advancing a second needle through the sleeve, tissue adjacent the opening in tissue, and into the second arm. The method further includes retrieving the second portion of the suture retained by the second arm with the second needle and withdrawing the second needle and the second portion of the suture proximally from the second arm and through tissue adjacent the opening in tissue.

In embodiments, advancing the first and second needles are performed simultaneously, retrieving the first and second portions of the suture are performed simultaneously, and withdrawing the first and second needles and first and second portions of the suture are performed simultaneously.

In embodiments, the method further includes tying off the first and second portions of the suture to close the opening in tissue.

In embodiments, sliding the sleeve distally includes incrementally locking the sleeve in position relative to the shaft.

BRIEF DESCRIPTION OF THE DRAWINGS

Various aspects and features of the presently disclosure are described hereinbelow with references to the drawings, wherein:

FIG. 3 is a side, perspective view of a surgical access device configured for use with the wound closure devices of the present disclosure;

FIG. 4 is a side, perspective view of a needle and sleeve assembly configured for use with the wound closure device of FIG. 1;

FIG. 5A is a side, perspective view illustrating the wound closure device of FIG. 1 inserted through the surgical access device of FIG. 3 and disposed in the retracted condition;

FIG. 5B is a side, perspective view illustrating the wound closure device of FIG. 1 inserted through the surgical access device of FIG. 3 and disposed in the deployed condition;

FIG. 8A is a longitudinal cross-sectional view illustrating the distal portion of the wound closure device of FIG. 1 including the needle and sleeve assembly of FIG. 4 disposed within an opening in tissue and having the needles deployed through tissue;

FIG. 8B is a longitudinal cross-sectional view illustrating the distal portion of the wound closure device of FIG. 1 including the needle and sleeve assembly of FIG. 4 disposed within the opening tissue, wherein the needles have been retracted to pull the suture through tissue;

FIG. 8C is a longitudinal cross-sectional view illustrating the distal portion of the wound closure device of FIG. 1, including the needle and sleeve assembly of FIG. 4, being withdrawn from the opening in tissue;

FIG. 9 is a cross-sectional view illustrating the suture tied off to close the opening in tissue;

FIG. 10A is a longitudinal cross-sectional view of another wound closure device provided in accordance with the present disclosure, disposed in a retracted condition;

FIG. 10B is a longitudinal cross-sectional view of the wound closure device of FIG. 10A, disposed in a deployed condition;

FIG. 15A is a side, perspective view of another wound closure device provided in accordance with the present disclosure, disposed in a retracted condition;

FIG. 15B is a side, perspective view of the wound closure device of FIG. 15A, disposed in a deployed condition and including a suture grasper extending therethrough;

FIG. 21 is a side view of a distal portion of another wound closure device provided in accordance with the present disclosure;

FIG. 22 is a side, perspective view of the wound closure device of FIG. 21;

FIG. 24 is a longitudinal cross-sectional view of a locking collar provided in accordance with the present disclosure and shown in use in conjunction with the wound closure device of FIG. 21;

FIG. 25A is a longitudinal cross-sectional view of another locking collar provided in accordance with the present disclosure and shown in use in conjunction with the wound closure device of FIG. 21;

FIG. 25B is a transverse cross-sectional view along section line "25B-25B" of FIG. 25A;

FIG. 29A is a side, perspective view of another suture grasper provided in accordance with the present disclosure, wherein the plunger of the suture grasper is disposed in a proximal position;

FIG. 29B is a side, perspective view of the suture grasper of FIG. 29A, wherein the plunger of the suture grasper is disposed in a distal position;

FIG. 30 is a side view of a distal portion of another wound closure device provided in accordance with the present disclosure including a replaceable suture member mounted thereon;

FIG. 31 is a side view of one of the arms of the wound closure device of FIG. 30 including the replaceable suture member removed therefrom;

FIG. 32 is a side view of a distal portion of another suture grasper provided in accordance with the present disclosure and configured for use with the wound closure device of FIG. 30;

FIG. 42 is a side, perspective view of another wound closure device provided in accordance with the present disclosure;

FIG. 43A is a longitudinal cross-sectional view of a distal portion of the wound closure device of FIG. 42, disposed in a retracted position;

FIG. 43B is a longitudinal cross-sectional view of a distal portion of the wound closure device of FIG. 42, disposed in a deployed position;

FIG. 44A is a top view of one of the arms of the wound closure device of FIG. 42 retaining a portion of suture thereon;

FIG. 44B is a side view of the arm of FIG. 44A retaining a portion of suture thereon;

DETAILED DESCRIPTION OF THE EMBODIMENTS

Figure 1:
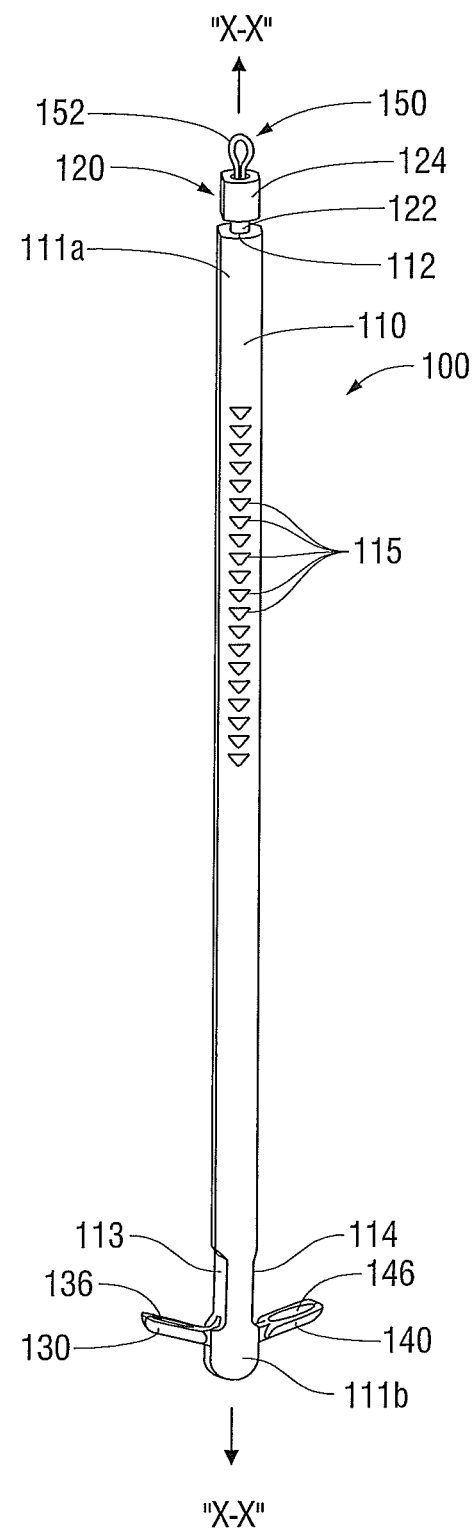
FIG. 1 is a side, perspective view of a wound closure device provided in accordance with the present disclosure.

In the figures and in the description that follows, in which like reference numerals identify similar or identical elements, the term "proximal" will refer to the end of the apparatus or portion thereof which is closest to the operator during use, while the term "distal" will refer to the end or portion which is farthest from the operator, as is traditional.

Figure 2:
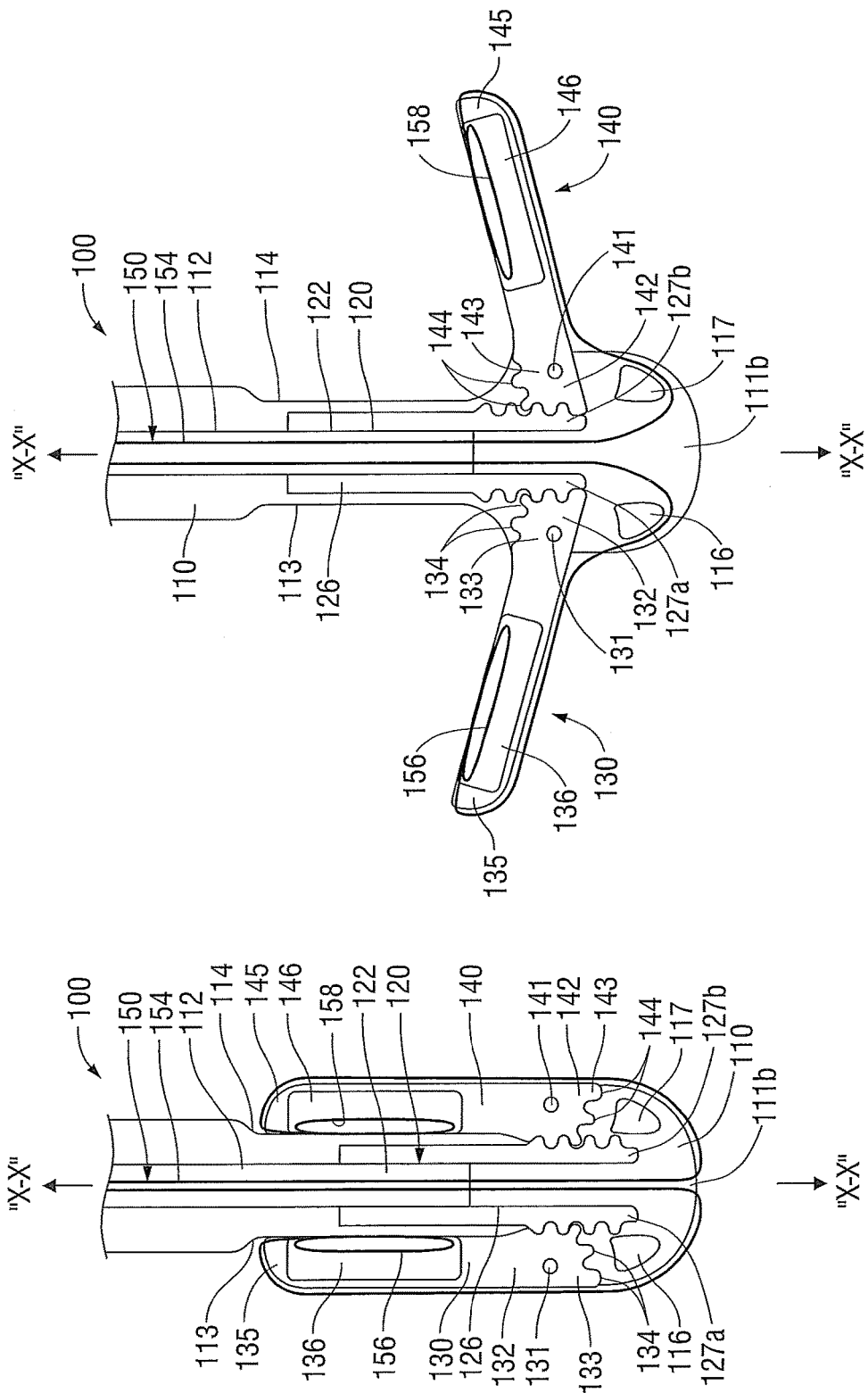
FIG. 2A is a longitudinal cross-sectional view of a distal portion of the wound closure device of FIG. 1, disposed in a retracted condition.
FIG. 2B is a longitudinal cross-sectional view of the distal portion of the wound closure device of FIG. 1, disposed in a deployed condition.

Turning to FIGS. 1-2B, a wound closure device provided in accordance with the present disclosure is shown generally as wound closure device 100. Wound closure device 100 includes an elongated shaft 110 defining proximal and distal regions 111a, 111b, respectively, and a longitudinal axis "X-X." A plunger 120 is slidably received within shaft 110 and extends longitudinally through shaft 110. A pair of selectively deployable arms 130, 140 is operably coupled to both shaft 110 and plunger 120 at distal region 111b of shaft 110. A suture 150 is operably coupled to wound closure device 100 and includes a intermediate portion 152 extending proximally from plunger 120 and shaft 110, a body portion 154 extending distally through plunger 120 and shaft 110, and first and second ends 156, 158 retained via first and second deployable arms 130, 140, respectively. First and second ends 156, 158 of suture 150 may defined a looped configuration formed via a cinch-knot, or any other suitable looped or other non-looped configuration. A pair of routing members 116, 117 is positioned in distal region 111b of shaft 110 and configured to route first and second ends 156, 158 of suture 150 from plunger 120, about routing members 116, 117, to the respective first and second arms 130, 140.

Shaft 110 is configured for insertion through an opening in tissue, e.g., wound, incision, or a naturally occurring orifice, such that distal region 111b of shaft 110 extends through the opening into an internal body cavity of the patient to allow for deployment of arms 130, 140 within the internal body cavity, while proximal region 111a of shaft 110 remains externally positioned relative to the opening to facilitate manipulation and/or actuation of wound closure device 100. Shaft 110 defines a longitudinal bore 112 extending therethrough. Bore 112 is configured to slidably receive plunger 120. Shaft 110 also includes first and second opposed cut-outs 113, 114 defined within the exterior surface of shaft 110 towards distal region 111b thereof for at least partially receiving arms 130, 140, respectively, when arms 130, 140 are disposed in the retracted position (FIG. 2A). As can be appreciated, such a feature reduces the maximum radial dimension of shaft 110 when arms 130, 140 are disposed in the retracted position (FIG. 2A) to facilitate insertion and removal of shaft 110 through the opening in tissue.

Arms 130, 140 are pivotably coupled to shaft 110 via pivot pins 131, 141 and are disposed in distal region 111b of shaft 110. Pivoting ends 132, 142 of arms 130, 140 each define a pinion member 133, 143 including a plurality of radially-disposed gear teeth 134, 144. Arms 130, 140 extend from pivoting ends 132, 142 to free ends 135, 145, respectively. Suture-retaining voids 136, 146 are defined within arms 130, 140 proximate free ends 135, 145, respectively. First and second ends 156, 158 of suture 150 may be releasably retained on arms 130, 140 adjacent to or within suture-retaining voids 136, 146 via adhesives, friction-fitting within slots defined about suture-retaining voids 136, 146 (see FIG. 13, for example), or in any other suitable fashion such as via any of the configurations detailed hereinbelow. Suture-retaining voids 136, 146, as will be described in greater detail hereinbelow, are configured for receiving needles 316, 318 (FIG. 4), respectively, to facilitate retrieval of first and second ends 156, 158 of suture 150 from arms 130, 140, and proximal withdrawal of first and second ends 156, 158 of suture 150 through tissue adjacent the opening in tissue.

Plunger 120, as mentioned above, is slidably received within shaft 110. More specifically, plunger 120 has an elongated rod 122 that is slidably received within longitudinal bore 112 defined through shaft 110. Rod 122 extends proximally from bore 112 of shaft 110 to an actuator member 124 disposed at the proximal end of rod 122. Actuator member 124 is configured to facilitate actuation of plunger 120. A gear rack 126 is disposed at the distal portion of rod 122. Gear rack 126 defines first and second linear gear-tooth segments 127a, 127b positioned adjacent respective first and second arms 130, 140 in meshed engagement with radially-disposed gear teeth 134, 144 of pinion members 133, 143 of arms 130, 140, respectively, such that distal translation of rod 122 through bore 112 and relative to arms 130, 140 effects rotation of arms 130, 140 relative to shaft 112 from the deployed position (FIG. 2B) to the retracted position (FIG. 2A), and such that proximal translation of rod 122 through bore 112 and relative to arms 130, 140 effects rotation of arms 130, 140 relative to shaft 112 from the retracted position (FIG. 2A) to the deployed position (FIG. 2B). Plunger 120 may be biased towards a proximal position such that arms 130, 140, in turn, are biased towards the deployed position (FIG. 2B), similarly as described below with respect to wound closure device 400 (FIGS. 10A-10B). Other biased configurations, or no biasing of arms 130, 140, are also contemplated.

Turning now to FIG. 3, an exemplary surgical access device configured for use with wound closure device 100 (FIG. 1), or any of the other wound closure devices provided in accordance with the present disclosure, is shown designated as surgical access device 200. Surgical access device 200 generally includes a proximal housing 210 and an elongated body 220 extending distally from proximal housing 210. Surgical access device 200 is configured for insertion into an opening in tissue such that proximal housing 210 is positioned proximally adjacent the opening, i.e., externally, while elongated body 220 extends distally though the opening and into the internal body cavity. Surgical access device 200 may include an inflation port (not shown) and one or more seal members (not shown) configured to facilitate insufflation of the internal body cavity and to maintain the internal body cavity in an insufflated state during use, e.g., during insertion, manipulation, and/or withdrawal of surgical instrumentation through access device 200. Any other suitable surgical access device may likewise be provided for use in accordance with the present disclosure.

With reference to FIG. 4, a needle and sleeve assembly provided in accordance with the present disclosure and configured for use with wound closure device 100 (FIG. 1)

is shown designated as needle and sleeve assembly 300. Needle and sleeve assembly 300 includes a needle assembly 310 and a sleeve 320. Needle assembly 310 includes a base member 312 defining a central aperture 314 configured to slidably receive shaft 110 of wound closure device 100 and is dimensioned to be complementary to shaft 110 (see FIG. 1). Needle assembly 310 further includes a pair of needles 316, 318 extending distally from base member 312 on either side of central aperture 314. Each needle 316, 318 defines a hooked or "J"-shaped distal end 317, 319 (FIG. 5E), although other configurations are also contemplated.

Continuing with reference to FIG. 4, sleeve 320 of needle and sleeve assembly 300 includes a body 322 having a proximal collar 324 and a bifurcated distal end 326 defining first and second fingers 327, 328 angled outwardly from body 322 and from one another. A central passageway 330 is configured to slidably receive shaft 110 of wound closure device 100 and dimensioned complementary to shaft 110 (see FIG. 1). Central passageway 330 extends longitudinally through proximal collar 324 and body 322 of sleeve 320. Proximal collar 324 includes a pair of opposed flexible ratchet tabs 332 pivotably disposed on proximal collar 324 to define opposed surfaces within central passageway 330. Teeth 333 of ratchet tabs 332 are configured to incrementally engage indentations 115 located on shaft 110 of wound closure device 100 to inhibit sleeve 320 from moving proximally as sleeve 320 is translated distally about shaft 110 of wound closure device 100 (see FIG. 1). In order to disengage teeth 333 from indentations 115, ratchet tabs 332 are flexed inwardly to displace teeth 333 from indentations 115, thus allowing sleeve 320 to be returned proximally. Body 322 further defines first and second needle lumens 334, 335 extending through proximal collar 324 on either side of passageway 330, through body 322, and first and second fingers 327, 328, respectively. Needle lumens 334, 335, as will be described in greater detail below, are configured to guide translation of needles 316, 318 through sleeve 320 and to direct needles 316, 318 towards suture-retaining voids 136, 146 of arms 130, 140 (FIG. 2B).

Turning now to FIGS. 5A-9, the use and operation of wound closure device 100, in conjunction with surgical access device 200 and needle and sleeve assembly 300, for closing an opening in tissue is described. As mentioned above, surgical access device 200 is typically utilized during a minimally-invasive surgical procedure to maintain the internal body cavity in an insufflated state during use and/or to facilitate the insertion, manipulation, and/or withdrawal of surgical instrumentation through access device 200 during the course of the surgical procedure.

Figure 5C:
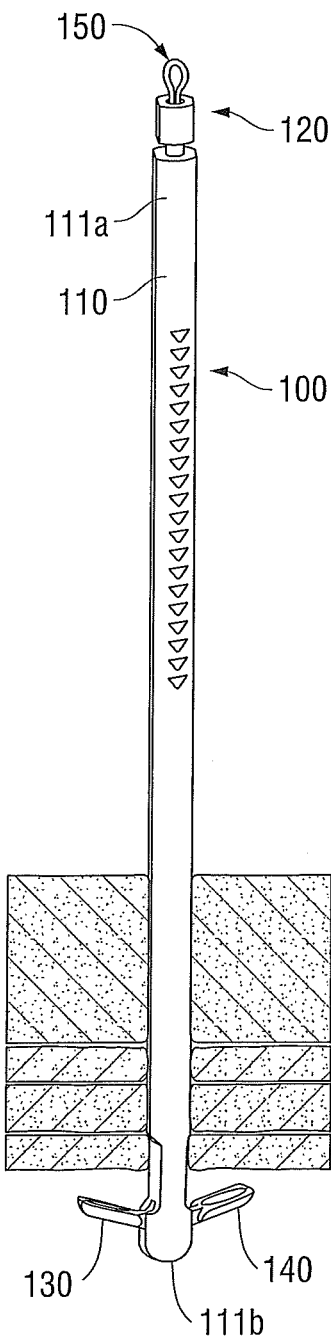
FIG. 5C is a side, perspective view illustrating the wound closure device of FIG. 1 after removal of the surgical access device from about the wound closure device.

Referring to FIGS. 5A-5C, when it is desired to close the opening in tissue, wound closure device 100 is inserted into through access device 200 with arms 130, 140 disposed in the retracted position, as shown in FIG. 5A. More specifically, prior to insertion, actuator member 124 of plunger 120 is depressed relative to shaft 110 to in order to rotate arms 130, 140 from the deployed position to the retracted position. Thus, with wound closure device 100 disposed in the retracted condition, wound closure device 100 may be inserted through access device 200 such that distal region 111*b* of shaft 110 of wound closure device 100 extends distally from access device 200 into the internal surgical site, while proximal region 111*a* of shaft 110 remains proximally of access device 200 and external to tissue. Once wound closure device 100 has been inserted through access device 200, actuator member 124 may be returned proximally relative to shaft 110 (or released, in embodiments where arms 130, 140 are biased towards the deployed position) to return arms 130, 140 to the deployed position, as shown in FIG. 5B. Thereafter, access device 200 may be withdrawn from the opening in tissue about wound closure device 100 (see FIG. 5C). More specifically, as the portion of wound closure device 100 disposed within and extending proximally from access device 200 defines a substantially uniform radial dimension, withdrawal of access device 200 about wound closure device 100 can be readily effected.

Figure 5D:
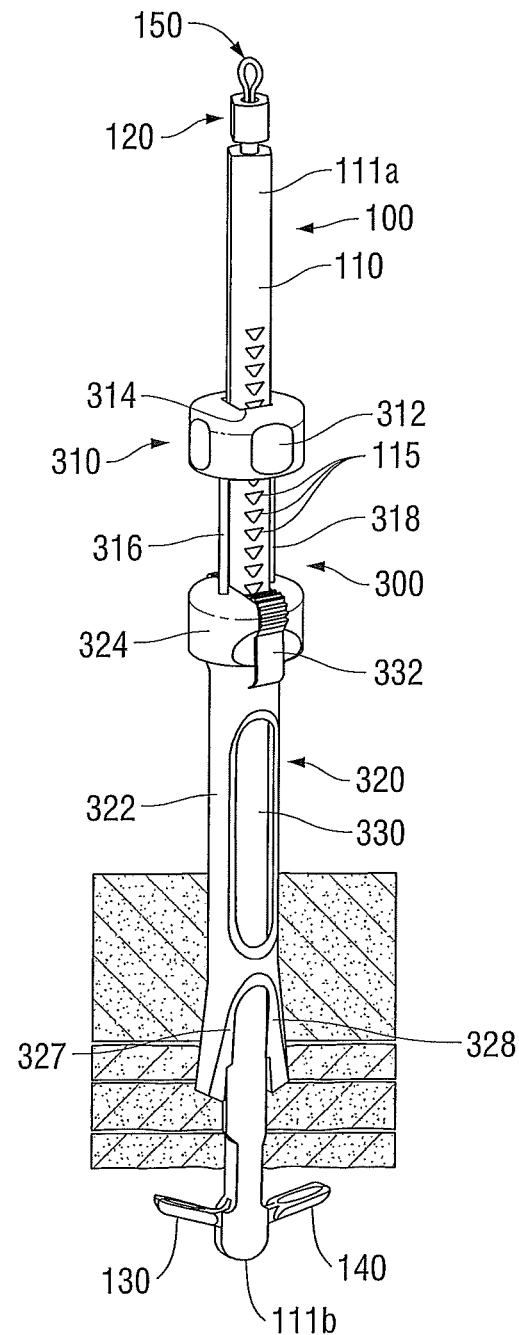
FIG. 5D is a side, perspective view of the wound closure device of FIG. 1 including the needle and sleeve assembly of FIG. 4 disposed thereabout, with the needles retracted.
Figure 5E:
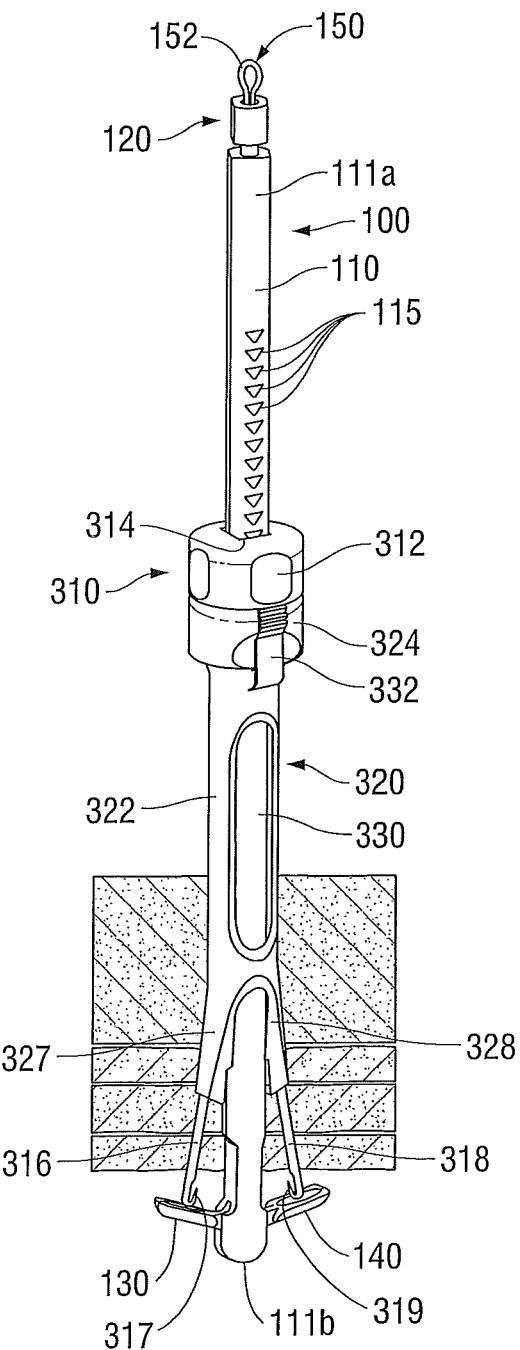
FIG. 5E is a side, perspective view of the wound closure device of FIG. 1 including the needle and sleeve assembly of FIG. 4 disposed thereabout, with the needles extended.

With reference to FIG. 5D, once access device 200 (FIGS. 5A-5B) has been withdrawn, sleeve 320 may be disposed about wound closure device 100 and slid distally about shaft 110 of wound closure device 100 until first and second fingers 327, 328 of sleeve 320 are positioned proximally adjacent to or partially extending into the opening in tissue, as shown in FIG. 5D. The particular positioning of first and second fingers 327, 328 of sleeve 320 relative to tissue may depend on the procedure being performed, the location of the opening in tissue, the patient's anatomy, the user's preference, and/or other factors. For some procedures, it has been found that extending sleeve 320 through the skin and fatty layers of tissue such that first and second fingers 327, 328 are positioned proximally adjacent the fascia and muscle layers of tissue is advantageous in that fascia and muscle layers are better suited to receive and retain a suture for closing the opening in tissue.

Continuing with reference to FIG. 5D, as sleeve 320 is slid distally about shaft 110 of wound closure device 100, ratchet tabs 332 of proximal collar 324 of sleeve 320 incrementally engage indentations 115 of shaft 110 to inhibit sleeve 320 from moving proximally. Further, the complementary configuration of central passageway 330 of body 322 of sleeve 320 relative to shaft 110 of wound closure device 100 ensures alignment of first and second fingers 327, 328 relative to first and second arms 130, 140, respectively. Sleeve 320 is translated distally along shaft 110 until the desired portion of tissue adjacent the opening is held or positioned between arms 130, 140 and fingers 327, 328.

Once sleeve 320 is positioned as desired, or prior thereto, base member 312 of needle assembly 310 is disposed about shaft 110 and slid distally about shaft 110 such that needles 316, 318 extend partially into, but not distally from, needle lumens 334, 335 (FIG. 8A) of sleeve 320. The complementary configuration of aperture 314 of base member 312 relative to shaft 110 ensures alignment of needles 316, 318 relative to needle lumens 334, 335 (FIG. 8A). With additional reference to FIG. 5E, with sleeve 320 and arms 130, 140 positioned such that tissue to be sutured is disposed therebetween, needle assembly 310 may be advanced further distally relative to shaft 110 and sleeve 320 such that needles 316, 318 extend from needle lumens 334, 335, through the tissue disposed between sleeve 320 and arms 130, 140, and into suture-retaining voids 136, 146 (FIG. 8A) of arms 130, 140.

Figure 6:
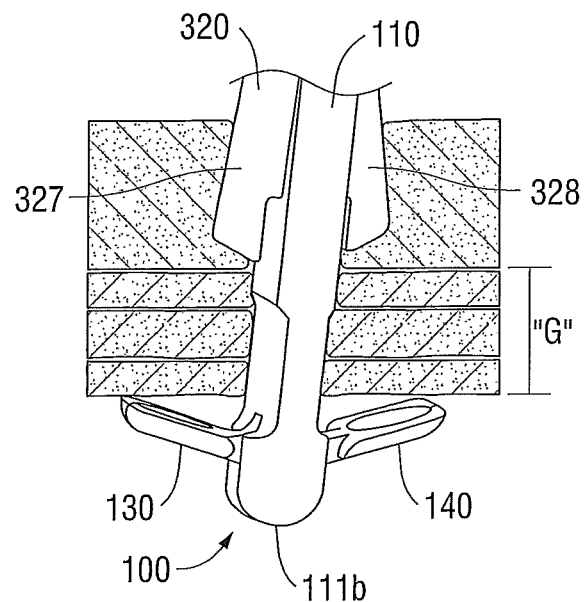
FIG. 6 is an enlarged, side, perspective view of the distal portion of the wound closure device of FIG. 1 including the needle and sleeve assembly of FIG. 4 disposed thereabout to define a first tissue gap therebetween.
Figure 7:
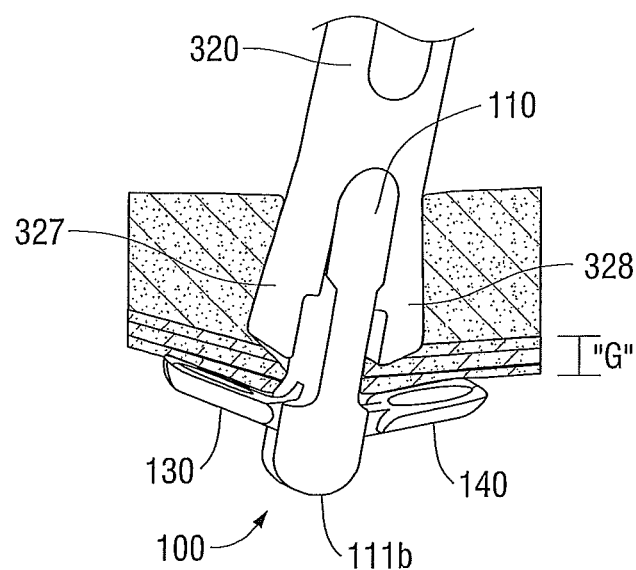
FIG. 7 is an enlarged, side, perspective view of the distal portion of the wound closure device of FIG. 1 including the needle and sleeve assembly of FIG. 4 disposed thereabout to define a second tissue gap therebetween.

Referring momentarily to FIGS. 6 and 7, as can be appreciated, depending on the thickness of tissue to be sutured, anatomical considerations, etc., sleeve 320 may be positioned more-distally, e.g., as in FIG. 6, or more-proximally, e.g., as in FIG. 7, to vary the gap distance "G" between fingers 327, 328 and arms 130, 140, respectively. As mentioned above, ratchet tabs 332 of proximal collar 324 of sleeve 320, in conjunction with indentations 115 of shaft 110 of wound closure device 100, allow for the user to set a desired gap distance "G" between fingers 327, 328 and arms 130, 140, respectively. Further, indicia or other visual markings may be provided on shaft 110 to allow the user to readily ascertain the gap distance "G."

Referring again to FIG. 5E, and with additional reference to FIG. 8A, needles 316, 318 are advanced through tissue into suture-retaining voids 136, 146 of arms 130, 140, respectively, sufficiently such that hooked distal ends 317, 319 of needles 316, 318 extend through and distally beyond first and second looped ends 156, 158 of suture 150. Once needles 316, 318 have been extended in this manner, the user may grasp intermediate portion 152 of suture 150, which extends proximally from plunger 120 and shaft 110, and translate suture 150 proximally. More specifically, suture 150 is translated proximally with sufficient urging such that looped ends 156, 158 of suture 150 are disengaged from arms 130, 140 and are cinched or otherwise held against needles 316, 318, as shown in FIG. 8A.

With additional reference to FIG. 8B, with ends 156, 158 of suture 150 cinched or held about needles 316, 318, needles 316, 318 may be retracted by translating base member 312 proximally relative to sleeve 320 until distal ends 317, 319 (FIG. 5E) of needles 316, 318 are retracted into needle lumens 334, 335 of sleeve 320. Retraction of needles 316, 318 catches first and second ends 156, 158 of suture 150 with respective distal ends 317, 319 (FIG. 5E) of needles 316, 318 such that first and second ends 156, 158 of suture 150 are pulled proximally through tissue and into needle lumens 334, 335 of sleeve 320. As can be appreciated, with suture 150 routed above distal region 111b of shaft 110 via routing members 116, 117, the above-detailed proximal movement of ends 156, 158 of suture 150 pulls intermediate portion 152 of suture 150 distally through wound closure device 100 and the opening in tissue (see FIG. 8C).

Referring additionally to FIGS. 8C and 9, once needles 316, 318 have been retracted and ends 156, 158 of suture 150 pulled proximally through tissue, arms 130, 140 of wound closure device 100 may be moved to the retracted position, e.g., via depressing actuator member 124 of plunger 120 (FIG. 5A). Thereafter, wound closure device 100, along with sleeve 320 (together or independently of one another), may be withdrawn from the opening in tissue, leaving suture 150 with a "U"-shaped configuration (FIG. 9) in tissue. In this configuration, ends 156, 158 of suture 150 extend proximally through tissue on either side of the opening and intermediate portion 152 of suture 150 extends across the opening on an internal side of tissue. With suture 150 in this configuration, ends 156, 158 may be tied off to close the opening in tissue (see FIG. 9).

Referring to FIGS. 10A and 10B, another wound closure device provided in accordance with the present disclosure is shown designated as wound closure device 400. Wound closure device 400 includes an elongated shaft 410, a plunger 420 slidably received within shaft 410 and extending longitudinally through shaft 410, and a pair of selectively deployable arms 430, 440 pivotably coupled to shaft 410. Similar to wound closure device 100 (FIG. 1), a suture 450 is operably coupled to wound closure device 400 such that an intermediate portion 452 extends proximally from plunger 420 and shaft 410, a body portion 454 extends distally through plunger 420 and shaft 410, and first and second ends 456, 458 are retained via first and second deployable arms 430, 440, respectively. Unless specifically contradicted hereinbelow, wound closure device 400 may incorporate any of the features of wound closure device 100 (FIG. 1), detailed above, and vice versa.

With continued reference to FIGS. 10A-10B, shaft 410 defines a central bore 411 extending longitudinally therethrough that is configured to slidably receive plunger 420. A chamber 412 is positioned at the proximal end of bore 411 in communication with bore 411. Chamber 412 defines an increased diameter as compared to bore 411. A biasing member 414 is positioned within chamber 412 and is inhibited from extending distally into bore 411 due to the reduced diameter of bore 411 as compared to chamber 412. A proximal end recess 415 defined within shaft 410 and disposed in communication with chamber 412 is configured to receive collar 425 of plunger 420 when plunger 420 is disposed in the depressed position (FIG. 10A). Shaft 410 further includes, similar to shaft 110 of wound closure device 100 (FIG. 1), first and second opposed cut-outs 416, 417 defined within the exterior surface of shaft 410 proximate the distal region thereof for at least partially receiving arms 430, 440, respectively, when arms 430, 440 are disposed in the retracted position (FIG. 10A).

Arms 430, 440 define pivoting ends 423, 442 adjacent respective pivot pins 431, 441. Pivoting ends 432, 442 of arms 430, 440 each define an angled cam surface 433, 443, the importance of which will be described in greater detail hereinbelow. Arms 430, 440 extend from pivoting ends 432, 442 to free ends 435, 445, respectively, that are configured to releasably retain the respective first and second ends 456, 458 of suture 450. Arms 430, 440 further include slots 436, 446 configured to route the respective first and second ends 456, 458 of suture 450 from the distal region of plunger 420 to free ends 435, 445 of arms 430, 440, respectively. Arms 430, 440 may be biased towards the deployed position (FIG. 10B), e.g., via torsion springs (not shown) disposed about pivot pins 431, 441 or in any other suitable manner.

Plunger 420 includes an elongated rod 422 that is slidably received within central bore 411 defined through shaft 410. Plunger 420 further includes an actuator member 424 having a collar 425 attached to a distal end thereof. Rod 422 extends distally from collar 425. Collar 425, as mentioned above, is configured for receipt within proximal end recess 415 of shaft 410 when plunger 420 is disposed in the depressed position (FIG. 10A). Rod 422 extends through biasing member 414 with biasing member 414 retained between collar 425 and the shoulder defined at the interface between chamber 412 and bore 411. As such, biasing member 414 biases collar 425 and, thus, plunger 420 proximally relative to shaft 410 (FIG. 10B).

A distal end cap 426 is disposed at the distal end of rod 422. More specifically, rod 422 extends distally through bore 411 and distally of pivot pins 431, 441 such that distal end cap 426 is positioned distally of and in contact with pivoting ends 432, 442 of arms 430, 440. In the depressed position of plunger 420, rod 422 extends further distally relative to arms 430, 440 such that distal end cap 426 is spaced distally from arms 430, 440, allowing arms 430, 440 to assume the deployed position (FIG. 10B) under bias of the torsion springs (not shown) or other suitable biasing mechanism. In the released position of plunger 420, distal end cap 426 is moved proximally, e.g., under the bias of biasing member 414, such that cam surfaces 428 of distal end cap 426 contact angled cam surfaces 433, 443 of arms 430, 440 to urge arms 430, 440 to pivot about pivot pins 431, 441 from the retracted position (FIG. 10A) to the deployed position (FIG. 10B). More specifically, the orientation of angled cam surfaces 433, 443 relative to cam surface 428 and the positioning of angled cam surfaces 433, 443 on the opposite side of pivot pins 431, 441 as compared to free ends 435, 445 of arms 430, 440, allow cam surfaces 428 of distal end cap 426 to urge arms 430, 440 to pivot about pivot pins 431, 441 from the retracted position (FIG. 10A) to the deployed position (FIG. 10B) as distal end cap 426 is translated proximally relative to shaft 410 under the bias of biasing member 414. Distal end cap 426 further defines a lumen configured to route first and second ends 456, 458 of suture 450 distally through end cap 426 to the respective first and second arms 430, 440.

The use and operation of wound closure device 400 is similar to that detailed above with respect to wound closure device 100 (FIG. 1). That is wound closure device 400 may be used in conjunction with surgical access device 200 and needle and sleeve assembly 300 for closing an opening in tissue, similarly as detailed above with respect to FIGS. 5A-9. Alternatively, wound closure device 400 may be used in conjunction with any other suitable suture retrieval device and/or access device, e.g., any of those detailed hereinbelow.

Figure 11A:
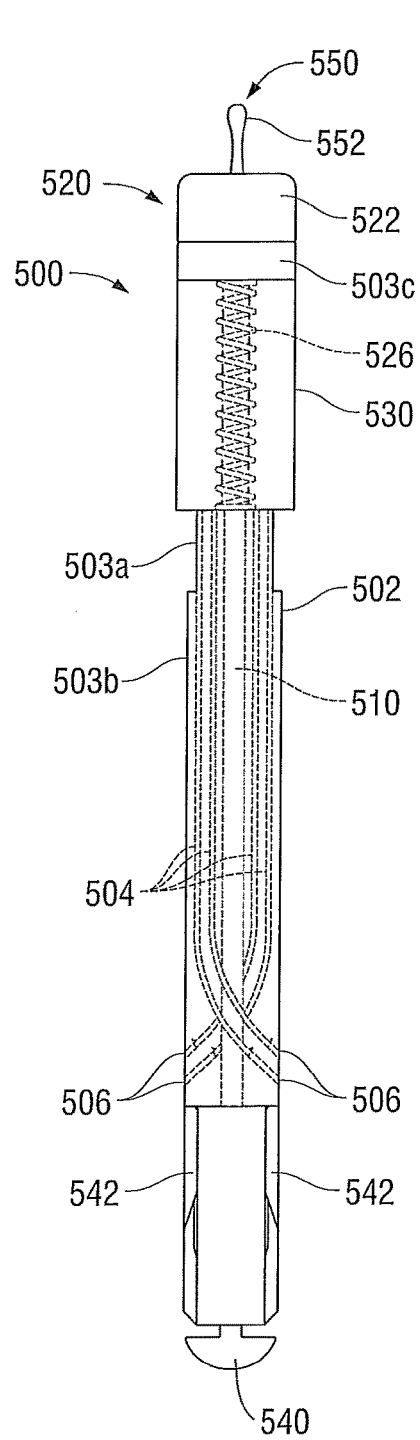
FIG. 11A is a side view of another wound closure device provided in accordance with the present disclosure, disposed in a retracted condition.

Referring to FIGS. 11A-13, another wound closure device provided in accordance with the present disclosure is shown designated as wound closure device 500. With reference to FIGS. 11A and 11B, wound closure device 500 includes an elongated tubular member 502, an elongated shaft 510 extending longitudinally through tubular member 502, a plunger 520 slidably received within shaft 510 and extending longitudinally through shaft 510, an actuator sleeve 530 slidably disposed about an annularly recessed proximal region 503a of elongated tubular member 502, and an end cap 540 disposed at the distal end of shaft 510 that includes four (4) selectively deployable arms 542. Similar to wound closure device 400 (FIGS. 10A and 10B), a suture 550 is operably coupled to wound closure device 500 such that an intermediate portion 552 extends proximally from plunger 520 and shaft 510, and a body portion (not shown) extends distally through plunger 520 and shaft 510. However, rather than providing two ends as with respect to wound closure device 400 (FIGS. 10A-10B), suture 550 defines four (4) ends 555, 556, 557, 558 (FIG. 12), e.g., via adjoining, knotting, braiding, etc. multiple sutures (or providing two or more separate sutures), each of which is retained via one of the deployable arms 542. Unless specifically contradicted hereinbelow, wound closure device 500 may incorporate any of the features of wound closure devices 100, 400 (FIGS. 1 and 10A-10B, respectively), detailed above, and vice versa.

Figure 11B:
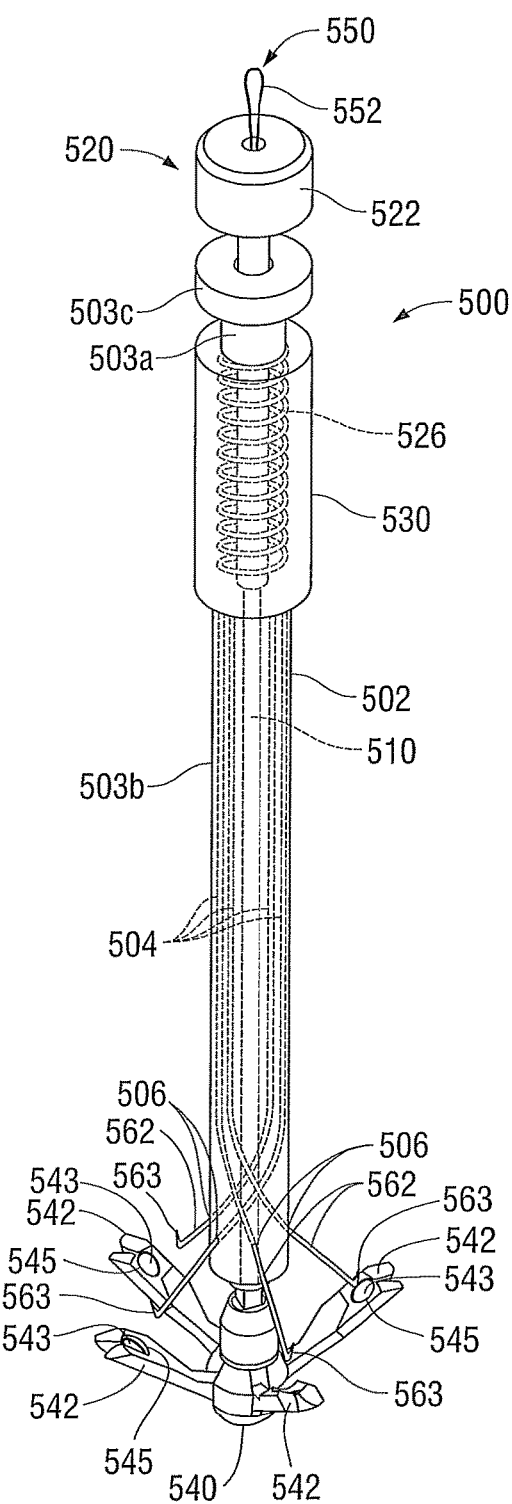
FIG. 11B is a perspective view of the wound closure device of FIG. 11A, disposed in a deployed condition.

With continued reference to FIGS. 11A-11B, shaft 510 defines a central bore (not explicitly shown) extending longitudinally therethrough that is configured to slidably receive the shaft of plunger 520, similarly as detailed above with respect to wound closure devices 100, 400 (FIGS. 1 and 10A-10B, respectively). End cap 540 is engaged to shaft 510 at the distal end of shaft 510 and, as mentioned above, includes four (4) selectively deployable arms 542 symmetrically disposed about shaft 510. Arms 542 are pivotably coupled to end cap 540 and are pivotable relative to end cap 540 between a retracted position (FIG. 11A) and a deployed position (FIG. 11B). Arms 542 will be described in greater detail hereinbelow.

Plunger 520 has an actuator 522 disposed at the proximal end of plunger 520. A rod of plunger 520 extends distally into end cap 540 and is operably coupled to arms 542 such that proximal translation of plunger 520 through and relative to shaft 510 effects pivoting of arms 542 from the retracted position (FIG. 11A) to the deployed position (FIG. 11B). More specifically, the rod of plunger 520 may be coupled to arms 542 in any suitable fashion for this purpose such as, for example, via a rack and pinion coupling, similarly are described above with respect to wound closure device 100 (FIG. 1), or via a cam surface coupling, similarly as described above with respect to wound closure device 400 (FIGS. 10A and 10B). Further, a biasing member 526 disposed within a chamber that communicates with the bore (not shown) of shaft 510 is provided to bias plunger 520 proximally, thus biasing arms 542 towards the retracted position (FIG. 11A), similarly as detailed above with respect to wound closure device 400 (FIGS. 10A and 10B).

Elongated tubular member 502 is disposed about shaft 510 and extends substantially along the length of shaft 510. However, shaft 510 extends further distally relative to elongated tubular member 502 such that elongated tubular member 502 is spaced-apart from the distal end of shaft 510 and end cap 540. As a result of this configuration, arms 542 may be closely approximated with shaft 510 when disposed in the retracted position (FIG. 11A), thereby defining a low-profile configuration. More specifically, in the retracted position, arms 542 do not extend beyond the outer radial dimension of elongated tubular member 502 to facilitate insertion and removal of wound closure device 500 through the opening in tissue.

Elongated tubular member 502 includes four (4) needle lumens 504 extending therethrough. Needle lumens 504 exit elongated tubular member 502 at four (4) equally-spaced openings 506 radially disposed about the outer peripheral surface of elongated tubular member 502 near the distal region thereof. Each opening 506 is positioned and oriented towards one of the arms 542 when arms 542 are disposed in the deployed position (FIG. 11B). Needle lumens 504 are radially disposed about shaft 510 and extend in generally parallel orientation relative to elongated tubular member 502 substantially along their lengths. However, the distal ends of needle lumens 504 define annular or helical configurations such that each lumen 504 communicates with one of the openings 506 defined within elongated tubular member 502.

Continuing with reference to FIGS. 11A-11B, a needle assembly is integrally provided with wound closure device 500. The needle assembly includes an actuator sleeve 530 slidably mounted about annularly recessed proximal region 503a of elongated tubular member 502 between a distal body portion 503b thereof and a proximal collar 503c thereof. The needle assembly further includes four (4) suture-retrieving needles 562 coupled to actuator sleeve 530 and slidably received within needle lumens 504 to move in conjunction with actuator sleeve 530. Each needle 562 defines a hooked or "J"-shaped distal end 563, although other configurations are also contemplated. Actuator sleeve 530 is slidable about annularly recessed proximal region 503 and relative to elongated tubular member 502 from a proximal position, corresponding to a storage position of needles 562, wherein needles 562 are fully disposed within lumens 504 (FIG. 11A), and a distal position, corresponding to an extended position of needles 562, wherein each needle 562 extends radially outwardly and distally from one of the openings 506 towards one of the arms 542 (FIG. 11B). Actuator sleeve 530 defines a low-profile configuration relative to distal body portion 503b of elongated tubular member 502 to facilitate removal of surgical access device 200 (FIG. 3) about wound closure device 500, similarly as detailed above. Wound closure device 500 may further include a handle (not shown) fixedly engaged to elongated tubular member 502 to facilitate sliding of actuator sleeve 530 relative to elongated tubular member 502 between the proximal and distal positions, e.g., via grasping both the handle and actuator sleeve 530 and sliding actuator sleeve 530 relative to the handle, and/or facilitating depression of actuator 522 relative to elongated tubular member 502, e.g., via grasping both the handle and actuator 522 and depressing actuator 522 relative to the handle. Alternatively or additionally, actuator sleeve 530 may be configured to rotate, e.g., 90 degrees, about elongated tubular member 502 between a locked position, wherein actuator sleeve 530 is fixed relative to elongated tubular member 502, e.g., to facilitate actuation of actuator 522, and an unlocked position, wherein actuator sleeve 530 is slidable about elongated tubular member 502, e.g., to permit actuation of actuator sleeve 530.

Figure 12:
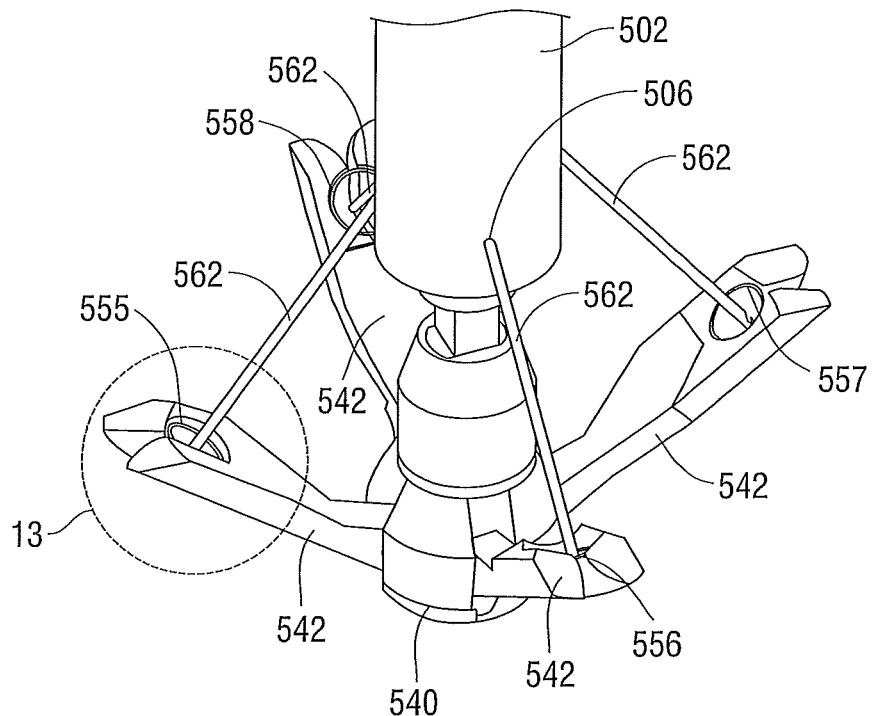
FIG. 12 is an enlarged, perspective view of the distal portion of the wound closure device of FIG. 11A, disposed in the deployed condition.
Figure 13:
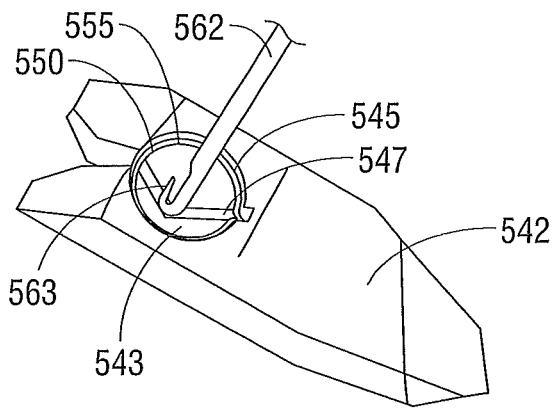
FIG. 13 is an enlarged, perspective view of the area of detail indicated as "13" in FIG. 12.

Referring additionally to FIGS. 12-13, each arm 542 defines a suture-retaining void 543 near the free end thereof. Annular slots 545 are defined about the inner surfaces of arms 542 that define suture-retaining voids 543. Each arm 542 further defines a linear slot 547 configured to route the ends 555, 556, 557, 558 of suture 550 from end cap 540 to the free ends of arms 542. The ends 555, 556, 557, 558 of suture 550 are looped about voids 543 and retained in position via engagement within annular slots 545. As such, needles 562 are insertable into voids 543 and through looped ends 555, 556, 557, 558, respectively, of suture 550. Openings 506 are positioned and oriented to direct needles 562 towards arms 542 such that, upon extension of needles 562, the hooked distal ends 563 of needles 562 extend into voids 543, as shown in FIGS. 12 and 13.

In use, similarly as detailed above with respect to wound closure device 100 (FIG. 1), wound closure device 500 is transitioned to the retracted position, e.g., via depression of actuator 522 relative to elongated tubular member 502, and is inserted into through an access device 200 (FIG. 3) positioned within an opening in tissue. Wound closure device 500 is capable of being used with access device 200 (FIG. 3) in that the low-profile configuration of wound closure device 500 allows access device 200 (FIG. 3) to be withdrawn about wound closure device 500, similarly as detailed above with respect to wound closure device 100 (FIG. 5A). However, it is also contemplated that wound closure device 500 be utilized without an access device 200 (FIG. 3), e.g., wound closure device 500 may be inserted after withdrawal of access device 200 (FIG. 3) from the opening in tissue.

Once wound closure device 500 has been inserted and access device 200 (FIG. 3) removed, actuator 522 may be released, allowing arms 542 to return under bias, to the deployed position. Alternatively, access device 200 (FIG. 3) may be removed after deployment of arms 542. With arms 542 deployed, wound closure device 500 may be manipulated such that the desired portion of tissue to be sutured is positioned between openings 506 defined within elongated tubular member 502 and arms 542. Next, actuator sleeve 530 is slid distally about annularly recessed proximal region 503a of elongated tubular member 502, e.g., via grasping actuator sleeve 530 and elongated tubular member 502 (or a handle (not shown) affixed thereto) and translating actuator sleeve 530 distally relative to elongated tubular member 502 to move needles 562 from the storage position, wherein needles 562 are fully disposed within lumens 504 (FIG. 11A), to the extended position, wherein needles 562 extend through tissue into a respective one of the suture-retaining voids 543 of arms 542 (see FIG. 13).

Once needles 562 have been advanced through tissue and into suture-retaining voids 543, the user may grasp intermediate portion 552 of suture 550 (FIGS. 11A and 11B) and translate suture 550 proximally with sufficient urging such that ends 555, 556, 557, 558 of suture 550 are disengaged from annular slots 545 and are cinched or otherwise held against needles 562. Once ends 555, 556, 557, 558 of suture 550 are cinched or held about needles 562, needles 562 may be retracted via proximal sliding of actuator sleeve 530 about annularly recessed proximal region 503a of elongated tubular member 502. As actuator sleeve 530 is slid proximally relative to elongated body 502, needles 562 are likewise translates proximally relative to elongated body 502 to catch ends 555, 556, 557, 558 of suture 550 with hooked distal ends 563 of needles 562. Needles 562 may then be retracted further proximally, e.g., via further proximal sliding of actuator sleeve 530, through tissue and into needle lumens 504 of elongated tubular member 502 to likewise pull ends 555, 556, 557, 558 of suture 550 through tissue and into needle lumens 504. Thereafter, arms 542, may be returned to the retracted position and wound closure device 400 may be withdrawn from the opening in tissue, leaving suture 550 positioned in a "U"-shaped configuration, similarly as detailed above with respect to wound closure device 100 (FIGS. 1-9), thus facilitating the tying off of ends 555, 556, 557, 558 of suture 550 to close the opening in tissue.

Figure 14:
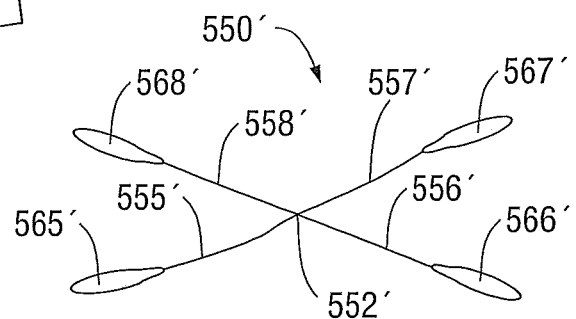
FIG. 14 is a top view of a four-legged suture provided in accordance with the present disclosure and configured for use with the wound closure device of FIG. 11A.

With reference to FIG. 14, another suture configured for use with wound closure device 500 (FIGS. 11A-11B) is shown as suture 550'. Suture 550' is similar to suture 550 (FIGS. 12-13) in that suture 550' defines four (4) ends 555', 556', 557', 558', e.g., via adjoining, knotting, braiding, etc. multiple sutures (or providing two or more separate sutures). However, it is also contemplated that sutures 550 (FIGS. 12-13), 550' be provided with greater or fewer ends, e.g., two (2) end for use with wound closure devices including two (2) deployable arms. Ends 555', 556', 557', 558' of suture 550' each define a looped configuration having a mesh portion 565', 566', 567', 568' extending across the opening defined by the loop. Mesh portions 565', 566', 567', 568' may be formed in any suitable fashion to permit insertion of a needle therethrough while inhibiting withdrawal of the needle, e.g., by catching the hooked ends of the needles (see FIG. 13). With additional reference to FIG. 12, in use, looped ends 555', 556', 557', 558' of suture 550' may be positioned within annular slots 545 of arms 542, similarly as detailed above with respect to suture 550. However, as meshed portions 565', 566', 567', 568' themselves provide the retention about needles 562, suture 550' need not extend through wound closure device 500. Rather, each end 555', 556', 557', 558' of suture 550' may extend through the linear slot 547 of a respective arm 542 such that the central portion 552' of suture 550' is positioned adjacent a distal surface of end cap 540 and such that each of the ends 555', 556', 557', 558' extends from center portion 552' to is respective arm 542.

Referring to FIGS. 15A-18B, and initially to FIGS. 15A-15B, another wound closure device provide in accordance with the present disclosure is shown generally as wound closure device 600. As detailed below, wound closure device 600 is configured for use with collar 700, suture grasper 800, cartridge 900 (FIGS. 16-18B), and/or any other suitable components such as any of those detailed herein. Wound closure device 600 includes an elongated shaft 610 defining proximal and distal regions 611a, 611b. A slider 612 is slidably received within the bifurcated proximal region 611a of shaft 110 and an end cap 614 is disposed at distal region 611b of shaft 610. Shaft 610 further includes a set of indentations 616 longitudinally arranged on either side thereof (only one of which is shown), and a plurality of angled needle lumens 617 extending therethrough, the importance of each of which will be detailed below.

Wound closure device 600 further includes a sleeve 618 disposed about elongated shaft 610 and extending from proximal region 611a to distal region 611b thereof. Sleeve 618 may be formed from first and second sleeve sections 619a, 619b configured to engage one another about shaft 610, e.g., via snap-fit engagement or other suitable releasable engagement. Alternatively, sleeve 618 may be integrally formed and/or permanently disposed about shaft 610 in any suitable fashion. Each sleeve section 619a, 619b is symmetrical relative to the other and includes a proximal portion that is operably positioned relative to slider 612, and a distal portion that is pivotably engaged to end cap 614 of shaft 610, e.g., via a post-recess engagement or other suitable pivotable engagement. Each sleeve section 619a, 619b defines a deployable arm 630, 640 proximate its distal portion. Each arm 630, 640 includes first and second spaced-apart living hinges 632, 634 and 642, 644, respectively, that permit arms 630, 640 to transition between a retracted position (FIG. 15A), corresponding to a proximal position of slider 612, wherein arms 630, 640 extend along and in generally parallel orientation relative to shaft 610 to facilitate insertion and removal of wound closure device 600, and a deployed position (FIG. 15B), corresponding to a distal position of slider 612, wherein slider 612 urges the proximal portion of sleeve 618 distally relative to the fixed distal end thereof to flex living hinges 632, 634 and 642, 644 such that arms 630, 640 extend outwardly from shaft 610 to facilitate retrieval of a portion of suture retained therein, as will be detailed below. Intermediate segments 636, 646 of arms 630, 640, which extend between the respective living hinges 632, 634 and 642, 644, each define a guide slit 638, 648 configured to guide a needle or other suture grasper towards the portion of suture retained on the respective arm 630, 640, as will be detailed below. Living hinges 632, 634 and 642, 644 may be configured such that arms 630, 640 are biased towards the retracted position, the deployed position, or define a bi-stable configuration. Arms 630, 640 may be configured to retain a portion of suture therein, similarly as detailed with respect to any of the other configurations herein, or may be configured for use in conjunction with a cartridge 900 (FIGS. 16-17) that retains the portion of the suture, as will be detailed below.

Each sleeve section 619a, 619b of sleeve 618 of wound closure device 600 further includes first and second elongated openings 622, 624. When sleeve 618 is engaged about shaft 610, the first opening 622 of each sleeve section 619a, 619b is aligned with one of the angled needle lumens 617 extending through shaft 610 to permit insertion of a needle or other suture grasper through shaft 610 and sleeve 618, tissue, and into one of the arms 630, 640. The second elongated opening 624 of each sleeve section 619a, 619b exposes indentations 616 of shaft 610 to allow for ratcheting of collar 700 thereabout, as detailed below.

With continued reference to FIGS. 15A and 15B, a collar configured for use with wound closure device 600 is shown generally as collar 700. Collar 700 includes a body 710 defining a longitudinal bore 712, and an annular rim 720 disposed at the distal end of body 710. Longitudinal bore 712 is configured to permit slidable positioning of collar 700 about shaft 610 and sleeve 618. Annular rim 720 defines a tissue-stop surface such that collar 700 may be slid distally about wound closure device 600 to grasp or hold tissue between annular rim 720 and arms 630, 640 (when arms 630, 640 are disposed in the deployed position). Annular rim 720 further defines a pair of slots 722, 724 configured to receive and direct a needle or other suture grasper through shaft 610 and sleeve 618, tissue, and into one of the arms 630, 640.

Collar 700 further includes a pair of opposed flexible ratchet tabs 730 pivotably disposed on body 710. Teeth 732 of ratchet tabs 730 are configured to incrementally engage indentations 616 formed on shaft 610 of wound closure device 600 to inhibit collar 700 from moving proximally as collar 700 is translated distally about shaft 610 and sleeve 618, similarly as detailed above with respect to sleeve 320 of needle and sleeve assembly 300 (FIG. 4).

Suture grasper 800, as shown in FIG. 15B, includes a handle portion 810 to facilitate grasping and manipulation of suture grasper 800, and an elongated needle 820 extending distally from handle portion 810. Needle 820 is configured for insertion through either slot 722, 724 of collar 720, the corresponding opening 622, 624 of sleeve 618, and a corresponding angled needle lumen 617 of shaft 610 such that needle 820 is directed through tissue and into the corresponding arm 630, 640 of sleeve 618. Needle 820 may define a "J" or hook-shaped distal end 822 to facilitate retrieval of a portion of suture, although other suitable configurations are also contemplated.

Referring to FIGS. 16-18B, cartridge 900 configured for use with wound closure device 600 is shown. Cartridge 900 is configured as a pre-loaded, single-use component such that cartridge 900 can be installed on wound closure device 600 in preparation for use and replaced with a new cartridge 900 for subsequent use. Alternatively, cartridge 900 may be reloadable. Cartridge 900 includes a base 910 and first and second arms 930, 940 coupled to base via living hinges 932, 934. Cartridge 900 may be formed from first and second cartridge portions 902, 904 configured to releasably engage one another, e.g., via snap-fit or other suitable releasable engagement, or may be permanently formed as a single component.

Base 910 of cartridge 900 defines a generally cylindrical configuration and includes an enclosed end 912 and an open end 914 cooperating to define a pocket 916. Pocket 916 is configured to receive an intermediate portion 952 of a suture 950 to inhibit tangling or catching of suture 950 during use. Base 910 may be releasably seated within shaft 610 of wound closure device 600 in the distal region thereof, as shown in FIGS. 16 and 17, and may be retained therein via friction-fitting or any other suitable releasable engagement.

Arms 930, 940, as mentioned above, are pivotably coupled to base 910 via living hinges 932, 942, and extend from hinges 932, 942 to free ends 934, 944. Living hinges 932, 942 permit arms 930, 940 to pivot relative to base 910 between a retracted position (FIG. 18A) and a deployed position (FIG. 18B), similar to and in conjunction with arms 630, 640 of wound closure device 600 (FIGS. 15A-15B). Once base 910 is seated within shaft 610 of wound closure device 600, arms 930, 940 may be releasably engaged to respective arms 630, 640 of sleeve 618 of wound closure device 600, e.g., via friction-fitting, snap-fitting, or other suitable releasable engagement. Alternatively or additionally, arms 930, 940 may be biased towards the deployed position such that arms 930 940 are biased into contact with arms 630, 640, respectively. Cartridge 900 may be installed on wound closure device 600 prior to installation of sleeve 618 thereabout, or when arms 630, 640 of sleeve 618 are disposed in the deployed position.

Each arm 930, 940 of cartridge 900 further includes a pair of spaced-apart retention members 936, 946, respectively, disposed thereon. Retention member 936, 946 may include spring arms, releasable clips, or any other suitable mechanism for releasably retaining a portion of suture 950 therein. More specifically, as shown in FIGS. 17 and 18B, retention members 936 of arm 930 retain first end 954 of suture 950 suspended therebetween, while retention members 946 of arm 940 retain second end 956 of suture 950 suspended therebetween.

Figure 16:
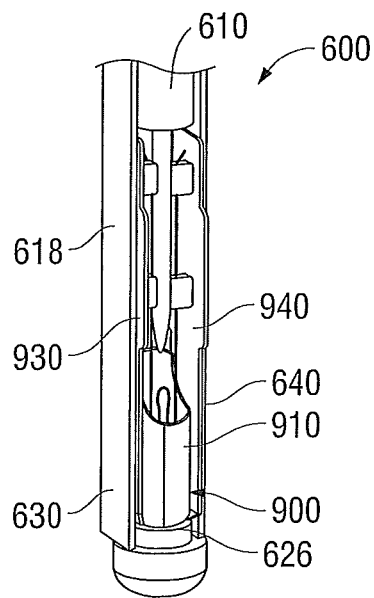
FIG. 16 is an enlarged, perspective view of the distal portion of the wound closure device of FIG. 15A, disposed in the retracted condition and including a replaceable cartridge mounted therein.
Figure 17:
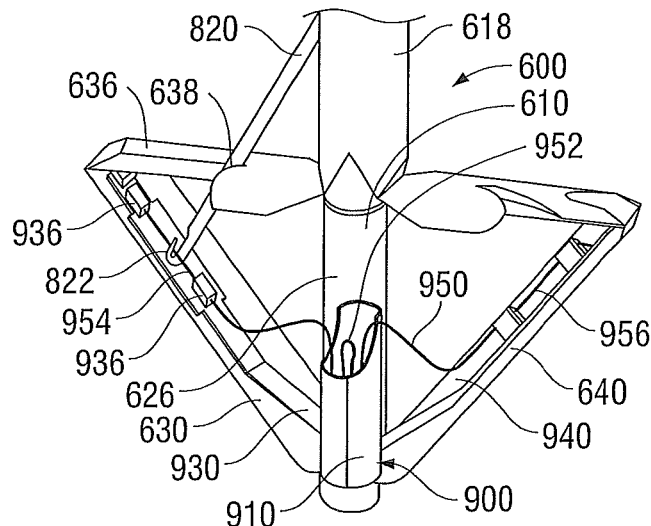
FIG. 17 is an enlarged, perspective view of the distal portion of the wound closure device of FIG. 15A, disposed in the deployed condition with the replaceable cartridge mounted therein and the suture grasper extending therethrough.
Figure 18A:
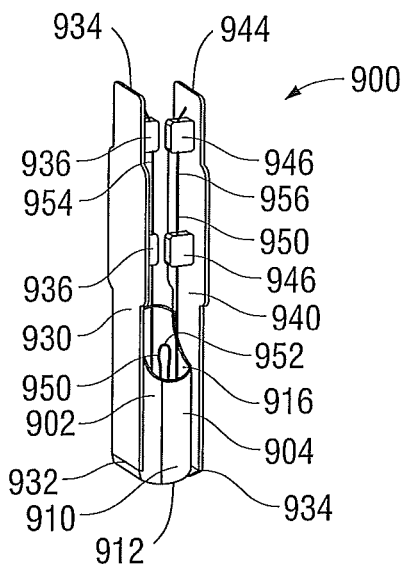
FIG. 18A is a side, perspective view of the replaceable cartridge, disposed in a retracted condition.
Figure 18B:
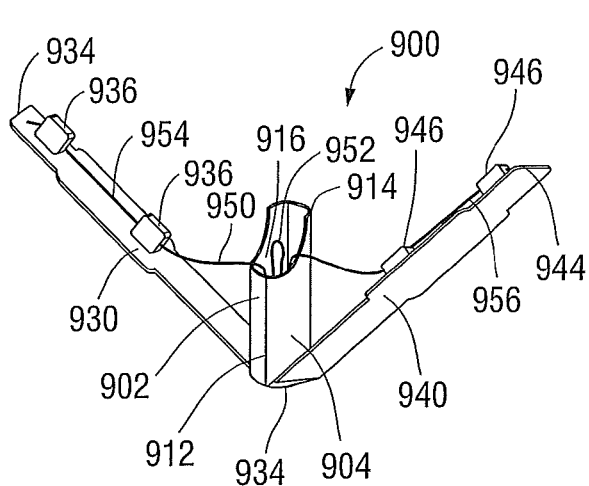
FIG. 18B is a side, perspective view of the replaceable cartridge, disposed in a deployed condition.

Referring to FIGS. 16 and 17 in particular, in use, with arms 630, 640 of sleeve 618 of wound closure device 600 disposed in the retracted position, arms 930, 940 of cartridge 900 are likewise disposed in the retracted position (FIG. 16) to facilitate insertion through an opening in tissue or access device and manipulation into position. Once positioned as desired, arms 630, 640 of wound closure device 600 may be deployed to likewise deploy arms 930, 940 of cartridge 900 (FIG. 17), e.g., as a result of the engagement therebetween and/or the bias of arms 930, 940 towards the deployed position. Once arms 930, 940 are deployed, needle 820 of suture grasper assembly 800 may be inserted through slot 724 of collar 720 (FIG. 15B), opening 624 (FIG. 15B) of sleeve 618, the corresponding angled needle lumen 617 (FIG. 15B) of shaft 610, tissue, and slit 638 of intermediate segment 636 of arm 630, such that needle 820 is directed between retention members 936 of arm 930, thereby readily enabling the retrieval of first end 954 of suture 950 using the hooked distal end 822 of needle 820. Needle 820 and first end 954 of suture 950 may then be withdrawn proximally through tissue and wound closure device 600 and a similar process may be effected on the opposite side to retrieve and withdraw the second end 956 of suture 950 proximally through tissue.

With reference to FIGS. 19A-19D, another suture grasper 1000 configured for use with wound closure device 600, any of the other wound closure devices detailed herein, or any suitable wound closure device, is shown generally as suture grasper 1000. Suture grasper 1000 includes an inner shaft 1010, a poly-furcated intermediate shaft 1020 having a plurality of spring fingers 1022 radially disposed about inner shaft 1010, an outer shaft 1030 disposed about intermediate shaft 1020, and a housing member 1040 disposed about outer shaft 1030. Inner shaft 1010 and housing member 1040 are fixed relative to one another, while both intermediate shaft 1020 and outer shaft 1030 are slidable relative to inner shaft 1010 and housing member 1040 and relative to one another.

Figure 19A:
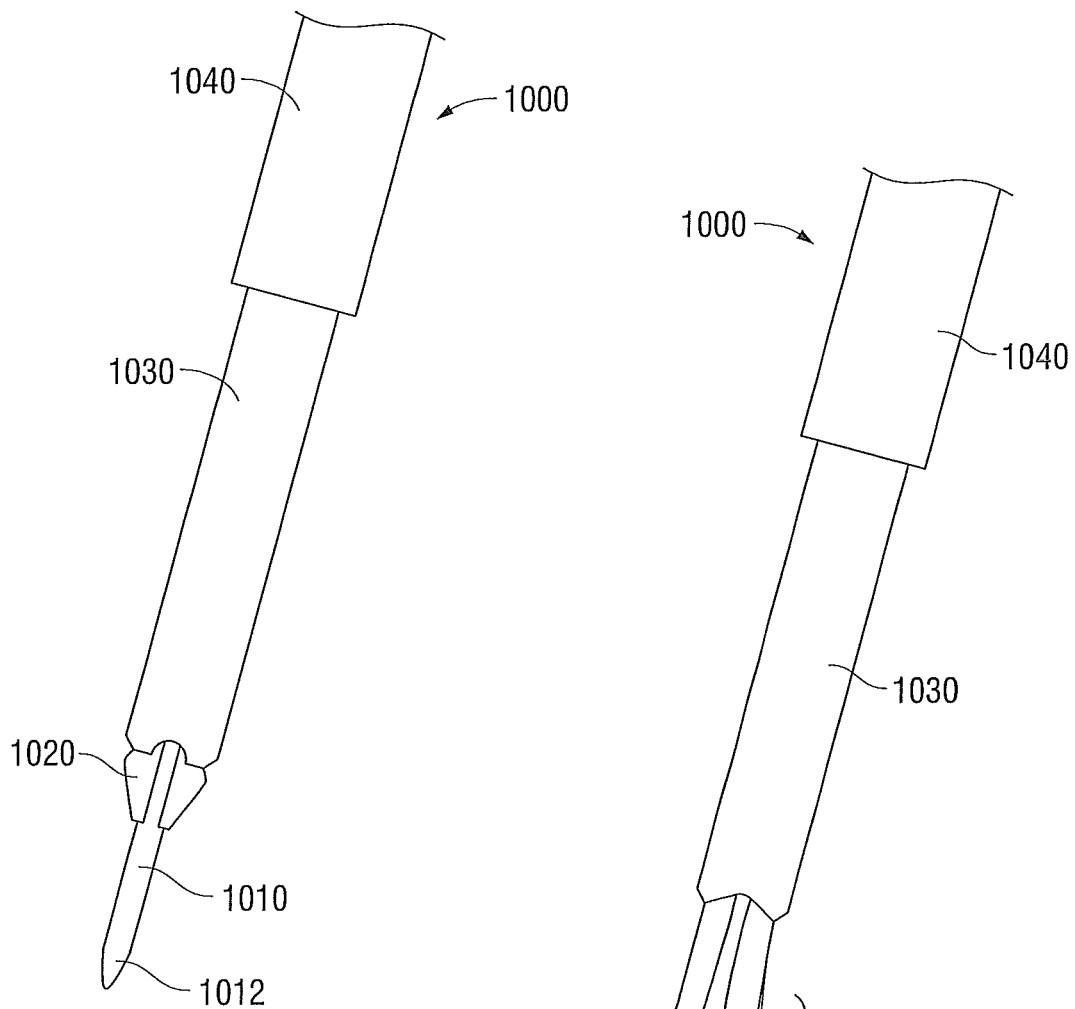
FIG. 19A is a side, perspective view of another suture grasper provided in accordance with the present disclosure, disposed in a penetrating condition.
Figure 19B:
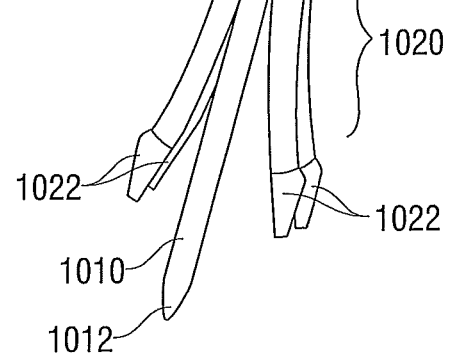
FIG. 19B is a side, perspective view of the suture grasper of FIG. 19A, disposed in an open condition.

Inner shaft 1010 defines a conical distal end 1012 configured to facilitate penetration of tissue, although other configurations are also contemplated. Spring fingers 1022 of intermediate shaft 1020 are biased towards a spread position, wherein spring fingers 1022 extend radially outwardly from inner shaft 1010 and one another (FIG. 19B). In a fully compressed or retracted position, spring fingers 1022 cooperate to define a generally tubular intermediate shaft 1020 having an inner diameter similar to the outer diameter of inner shaft 1010 (FIG. 19A). Outer shaft 1030 defines an inner diameter larger than the outer diameters of inner shaft 1010 and intermediate shaft 1020 but sufficiently small so as to compress spring fingers 1022 towards or to their fully compressed position when disposed about spring fingers 1022. Housing member 1040 may be configured to facilitate grasping and manipulation of suture grasper 1000 and may further include first and second actuators (not shown) for actuating intermediate shaft 1020 and outer shaft 1030, respectively.

Figures 19C, 19D:
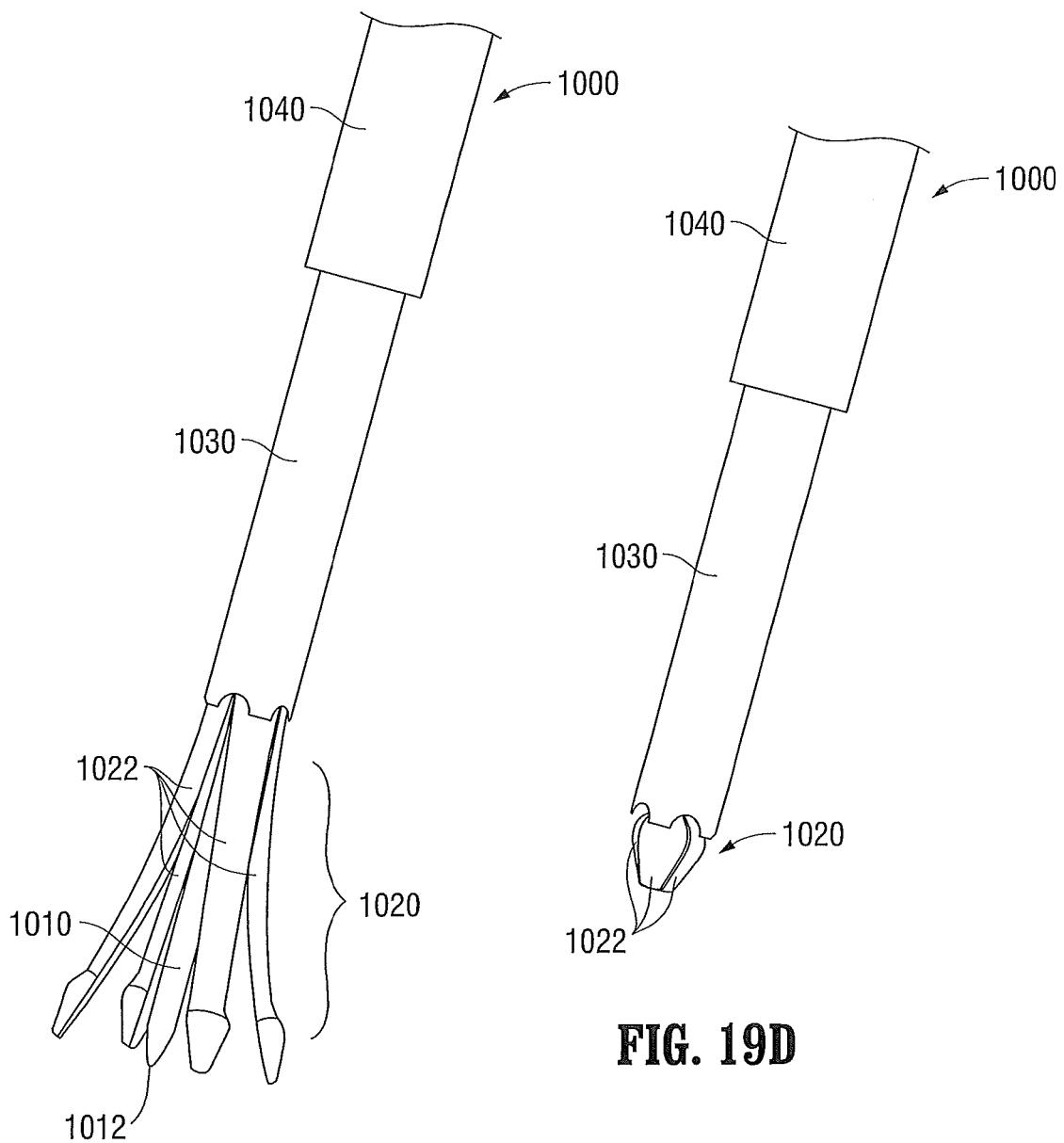
FIG. 19C is a side, perspective view of the suture grasper of FIG. 19A, disposed in an extended condition.
FIG. 19D is a side, perspective view of the suture grasper of FIG. 19A, disposed in a grasping condition.

Suture grasper 1000 is configured to transition among four (4) configurations: a penetration configuration, as shown in FIG. 19A, wherein suture grasper 100 defines a low-profile configuration with conical distal end 1012 of inner shaft 1010 exposed to facilitate penetration of tissue; an open configuration, as shown in FIG. 19B, wherein intermediate shaft 1020 is maintained in position while outer shaft 1030 is moved proximally such that spring fingers 1022 are permitted to extend radially outwardly, under bias, from inner shaft 1010; an extended configuration, as shown in FIG. 19C, wherein both intermediate shaft 1020 and outer shaft 1030 are moved distally such that spring fingers 1022 extend to distal end 1012 of inner shaft 1010; and a grasping configuration, as shown in FIG. 19D, wherein outer shaft 1030 is fully extended to the distal end 1012 of inner shaft 1010 to compress spring fingers 1022 towards or to their fully compressed position about inner shaft 1010. The use of suture grasper 1000 is detailed below.

Spring fingers 1022 of suture grasper 1000 may further include inwardly-extending barb features (not explicitly shown), or other suitable retention features (such as any of those detailed herein or any other suitable retention feature) to facilitate retaining a portion of suture between spring fingers 1022 and inner shaft 1010. In such embodiments, inner shaft 1010 may include complementary recesses (not explicitly shown) defined therein that are configured to receive the barb features of spring fingers 1022 in mating engagement to retain the suture therebetween.

With reference to FIGS. 20A-20D, the use of suture grasper 1000 in conjunction with wound closure device 600 and cartridge 900 is described, although suture grasper 1000 may alternatively be used alone or with any other wound closure device(s). Initially, wound closure device 600 is inserted through an opening in tissue or access device, manipulated into position, and arms 630, 640 (FIG. 15B) are deployed to likewise deploy arms 930, 940 of cartridge 900 (FIG. 15B).

Figure 20A:
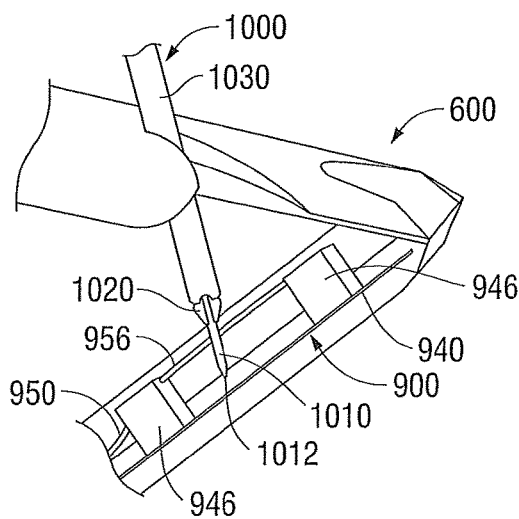
FIG. 20A is an enlarged, side, perspective view of the distal portion of the wound closure device of FIG. 15A including the suture grasper of FIG. 19A extending therethrough in the penetrating condition.
Figure 20B:
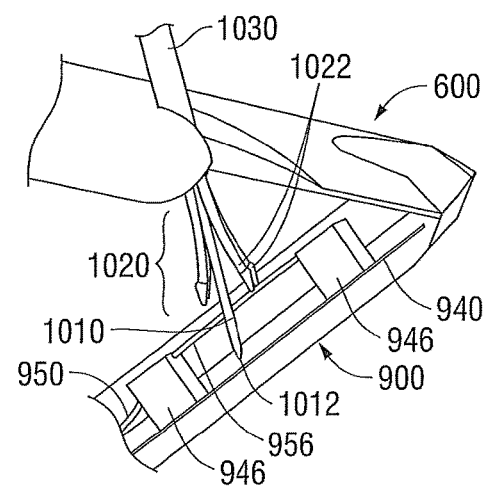
FIG. 20B is an enlarged, side, perspective view of the distal portion of the wound closure device of FIG. 15A including the suture grasper of FIG. 19A extending therethrough in the open condition.
Figure 20C:
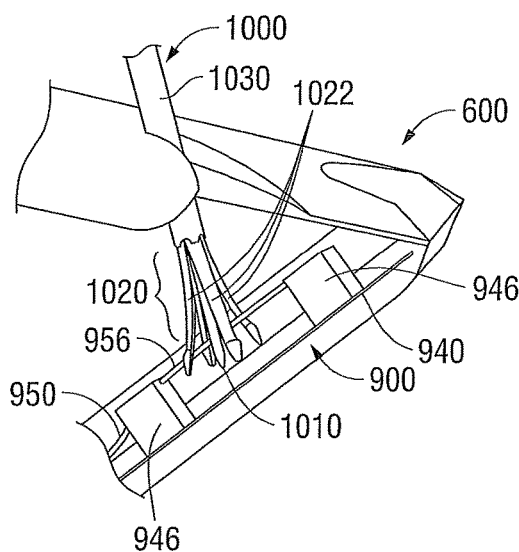
FIG. 20C is an enlarged, side, perspective view of the distal portion of the wound closure device of FIG. 15A including the suture grasper of FIG. 19A extending therethrough in the extended condition.

Next, as shown in FIG. 20A, with suture grasper 1000 disposed in the penetration configuration, suture grasper 1000 is advanced through wound closure device 600 and tissue, lead by conical distal end 1012 of inner shaft 1010, until distal end 1012 of inner shaft 1010 is positioned between the retention members 946 of the corresponding arm 940 of cartridge 900 adjacent the end 956 of suture 950 retained thereon. Once this position has been achieved, as shown in FIG. 20B, suture grasper 1000 may be transitioned to the open configuration, wherein spring fingers 1022 extend radially outwardly, under bias, from inner shaft 1010, and then to the extended configuration, as shown in FIG. 20, wherein spring fingers 1022 extend to distal end 1012 of inner shaft 1010 such that the end 956 of suture 950 is disposed between at least one of the spring fingers 1022 and inner shaft 1010.

Figure 20D:
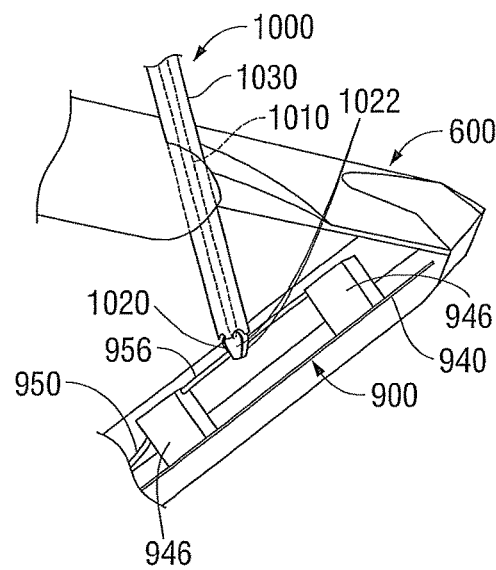
FIG. 20D is an enlarged, side, perspective view of the distal portion of the wound closure device of FIG. 15A including the suture grasper of FIG. 19A extending therethrough in the grasping condition.

Thereafter, suture grasper 1000 may be transitioned to the grasping configuration, as shown in FIG. 20D, wherein outer shaft 1030 compresses spring fingers 1022 about inner shaft 1010 to retain the end 956 of suture 950 therebetween. Suture grasper 1000, with end 956 of suture 950 retained thereon, may then be withdrawn proximally through tissue and wound closure device 600 and a similar process may be effected on the opposite side to retrieve and withdraw the other end of suture 950 proximally through tissue.

Referring to FIGS. 21-22, another wound closure device provided in accordance with the present disclosure is shown generally as wound closure device 1100. Wound closure device 1100 includes an elongated shaft 1110 defining proximal and distal regions 1111a, 1111b, respectively, a plunger 1120 slidably received within shaft 1110 and extending longitudinally through shaft 1110, and a pair of selectively deployable arms 1130, 1140 operably coupled to shaft 1110 and plunger 1120 at respective distal regions 1111b, 1121 of shaft 1110 and plunger 1120.

Shaft 1110 is configured for insertion through a wound or other opening in tissue and defines a longitudinal bore 1112 extending therethrough that is configured to slidably receive plunger 1120. First and second arms 1130, 1140 are coupled to distal region 1111b of shaft 1110 on opposite sides thereof via living hinges 1132, 1142. Shaft 1110 further defines a plurality of angled needle lumens 1114 configured to direct a needle inserted therethrough to a corresponding arm 1130, 1140. Although only two needle lumens 1114 are shown, it is contemplated that a plurality of pairs of angled needle lumens 1114 be provided at different longitudinal positions along shaft 1110 for use with various tissue thicknesses and/or tissue layer structures.

Plunger 1120 includes a distal region 1121 that extends distally beyond distal region 111b of shaft 1110. The proximal region (not shown) of plunger 1120 may include an actuator (not shown) for selectively translating plunger 1120 through and relative to bore 1112 of shaft 1110, similarly as detailed above with respect to wound closure device 100 (FIG. 1). First and second arms 1130, 1140 are coupled to distal region 1121 of plunger 1120 via a pivot pin 1122, although separate pivot pins and/or other pivotable engagement structures, e.g., living hinges, are also contemplated.

Each arm 1130, 1140 defines first and second segments 1134, 1136 and 1144, 1146, respectively, interconnected via a living hinge 1138, 1148, respectively. First segments 1134, 1144 are coupled to shaft 1110 via living hinges 1132, 1142, respectively, and define openings 1139, 1149 configured to retain, suspend, seat, receive, and/or otherwise provide for the depositing or retrieval of portion of suture. Various embodiments of such are detailed below. Second segments 1136, 1146 are coupled to distal region 1121 of plunger 1120 via pivot pin 1122.

As a result of the above-detailed configuration of arms 1130, 1140 with respect to shaft 1110 and plunger 1120, plunger 1120 may be translated through and relative to shaft 1110 between a distal position and a proximal position. The distal position corresponds to the retracted position of arms 1130, 1140 (FIG. 21), wherein arms 1130, 1140 are generally disposed within the outer radial dimension of shaft 1110 with the respective segments 1134, 1136 and 1144, 1146 thereof disposed in linear orientation. The proximal position corresponds to the deployed position of arms 1130, 1140 (FIG. 22), wherein arms 1130, 1140 are pivoted about living hinges 1132, 1142 and pivot pin 1122 and wherein segments 1134, 1136 and 1144, 1146 are pivoted relative to one another about living hinges 1138, 1148, respectively, such that segments 1134, 1144 are positionable adjacent an internal surface of tissue and such that openings 1139, 1149 are disposed in alignment with angled needle lumens 1114. Living hinges 1132, 1142, 1138, 1148 and pivot pin 1122 may be configured to bias arms 1130, 1140 towards the deployed position, the retracted position, or may define a bi-stable configuration. The use of wound closure device 1100 may be similar to that of wound closure device 100 (FIG. 1), detailed above.

Figure 23:
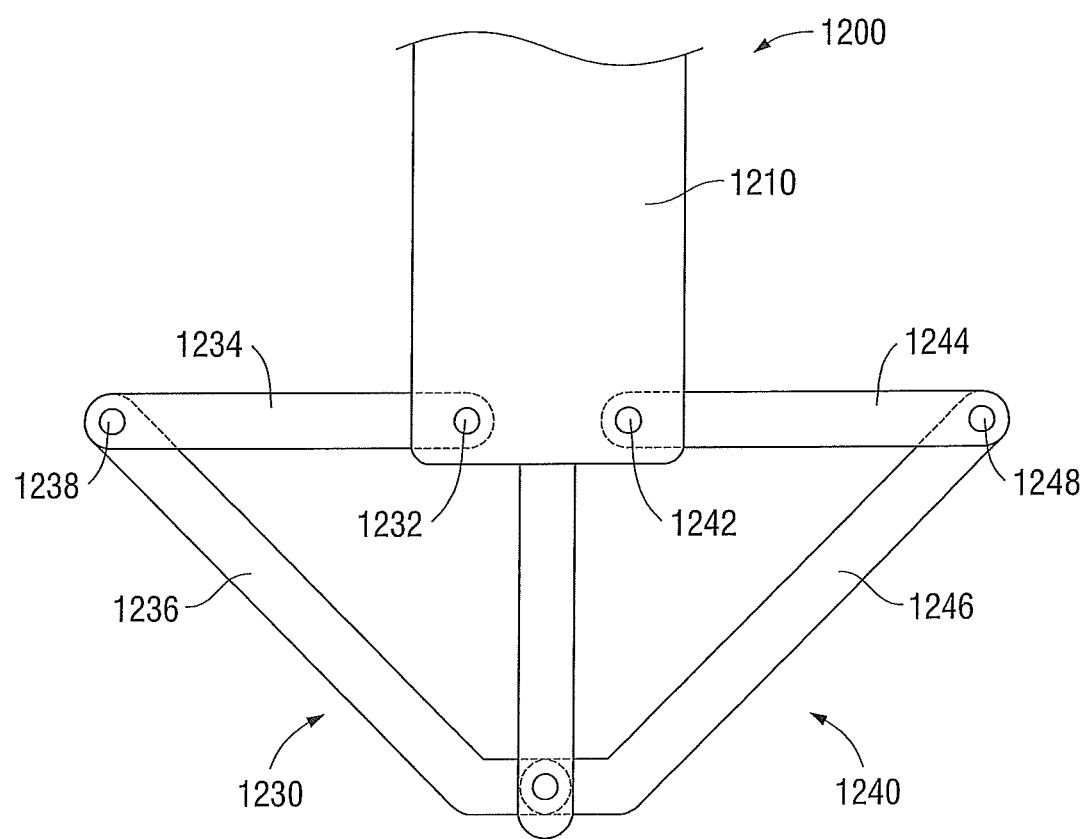
FIG. 23 is a side view of a distal portion of another wound closure device provided in accordance with the present disclosure.

Turning now to FIG. 23, another wound closure device provided in accordance with the present disclosure is shown generally as wound closure device 1200. Wound closure device 1200 is similar to wound closure device 1100 (FIGS. 21-22) except that, rather than living hinges coupling first and second arms 1230, 1240 to shaft 1210, pivot pins 1232, 1242 are provided and, rather than living hinges coupling the segments 1234, 1236 and 1244, 1246 of arms 1230, 1240 to one another, pivot pins 1238, 1248, respectively, are provided. Wound closure device 1200 may otherwise be configured similar to wound closure device 1100 (FIGS. 21-22) in both structure and operation. Wound closure device 1200 and/or wound closure device 1100 (FIGS. 21-22), may further include a plurality of teeth 1226 longitudinally disposed along a portion thereof on either side thereof (see FIG. 24).

With reference to FIG. 24, a collar configured for use with wound closure device 1200 is shown generally as collar 1300. Collar 1300 is similar to collar 700 (FIGS. 15A-15B) any generally includes a body 1310 defining a longitudinal bore 1312, an annular rim 1320 disposed at the distal end of body 1310, and a pair of opposed flexible ratchet tabs 1330 pivotably disposed on body 1310. Collar 1300 is slidably positionable about shaft 1210 of wound closure device 1200. Annular rim 1320 defines a distally-facing tissue-stop surface such that collar 1300 may be slid distally about wound closure device 1300 to grasp tissue between annular rim 1320 and arms 1230, 1240. Each ratchet tab 1330 includes a tooth 1332 extending into longitudinal bore 1312 and configured for engagement between any adjacent pair of teeth 1226 defined on shaft 1210 to lock collar 1300 in a desired position to define a suitable tissue gap "G" between annular rim 1320 and arms 1230, 1240, depending on the thickness of tissue, structure of tissue layers, etc. Grasping or retaining tissue between annular rim 1320 and arms 1230, 1240 also serves to stabilize wound closure device 1200 within the opening in tissue. In order to release or unlock ratchet tabs 1330, spring legs 1334 of ratchet tabs 1330 are flexed inwardly such that teeth 1332 are pivoted out of engagement between teeth 1226 of shaft 1210, thus permitting collar 1300 to be returned proximally. Upon release of spring legs 1334, teeth 1332 are pivoted, under bias of spring legs 1334, back into engagement with teeth 1226 of shaft 1210, e.g., towards the locked position.

FIGS. 25A-25B show another collar 1400 provided in accordance with the present disclosure and configured for use with wound closure device 1200 (or other suitable device) for grasping or maintaining tissue between collar 1400 and arms 1230, 1240 of wound closure device 1200. Collar 1400 generally includes a body 1410 defining a longitudinal bore 1412, and a rotatable lock member 1430 pivotably disposed on body 1410. Collar 1400 is slidably positionable about shaft 1210 of wound closure device 1200 and may further include an annular rim (not shown) similar to annular rim 1320 of collar 1300 (FIG. 24). Body 1410 of collar 1400 may define a "C"-shaped configuration, as shown in FIG. 25B, or may define a full annular configuration.

Rotatable lock member 1430 is pivotably coupled to body 1410 and has a protruding portion 1432 rotatable between an unlocked position (FIG. 25A), where protruding portion 1432 is displaced from bore 1412 to permit collar 1400 to slide about shaft 1210, and a locked position, wherein protruding portion 1432 extends into bore 1412 to frictionally engage shaft 1210, thereby locking lock collar 1400 in position about shaft 1210 between the internal surface of body 1410 that defines bore 1412 and protruding portion 1432 of lock member 1430. Thus, once collar 1400 is positioned to define the desired gap distance between collar 1400 and arms 1230, 1240, lock member 1430 may be rotated from the unlocked position to the locked position to lock collar 1400 in position.

Figure 26:
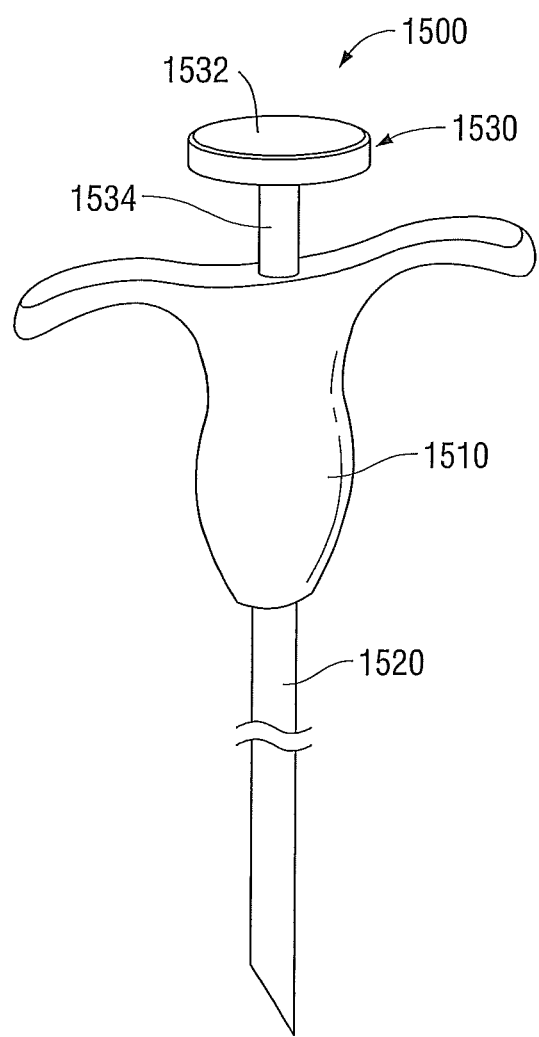
FIG. 26 is a side, perspective view of another suture grasper provided in accordance with the present disclosure.
Figures 27, 28:
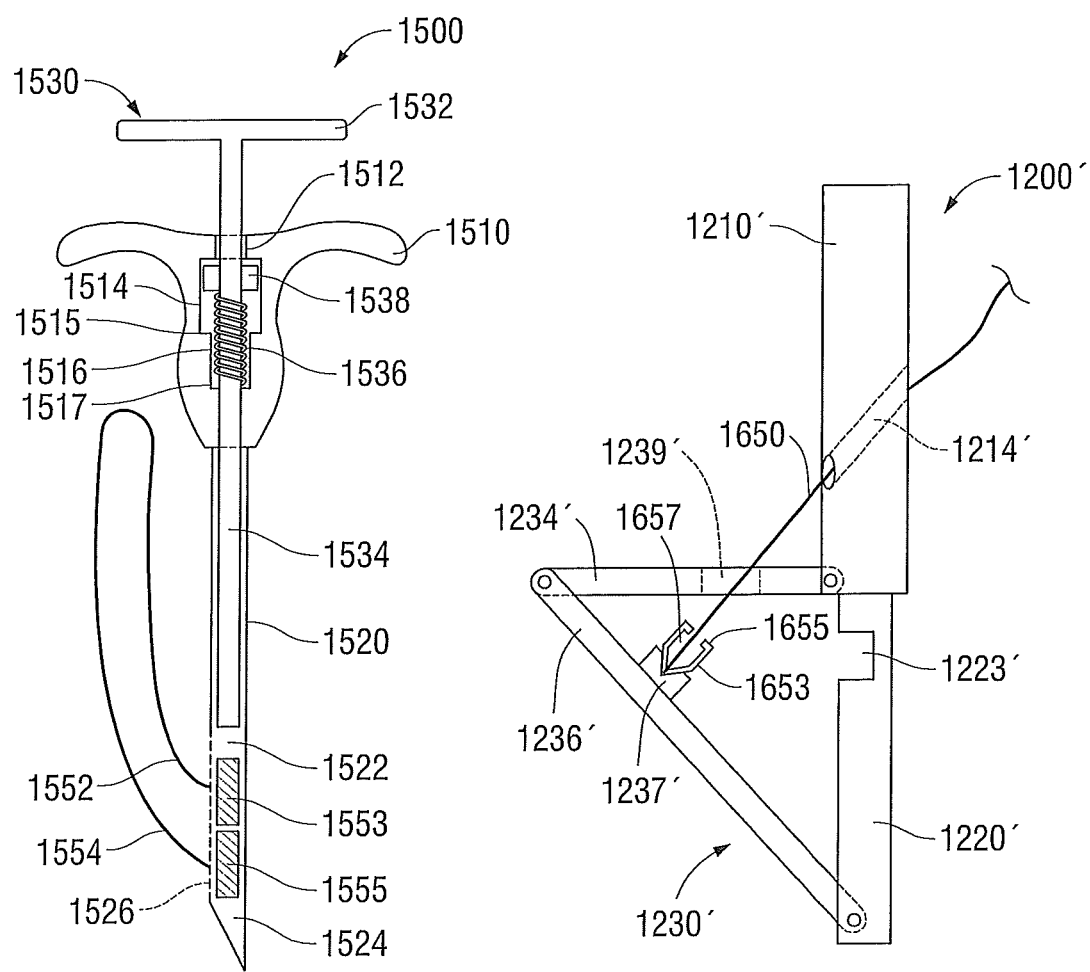
FIG. 27 is a longitudinal cross-sectional view of the suture grasper of FIG. 26 including a suture member mounted therein.
FIG. 28 is a side view of a distal end of another wound closure device provided in accordance with the present disclosure retaining a portion of a suture thereon.

Referring to FIGS. 26-27, in conjunction with FIG. 22, another suture passer 1500 configured for use with wound closure device 1100 (or any other suitable wound closure device) is shown generally as suture passer 1500. Suture passer 1500 generally includes a handle portion 1510, an elongated body 1520 extending distally from handle portion 1510, and a plunger 1530. Plunger 1530 includes an actuator 1532 extending proximally from handle portion 1510 and an actuation shaft 1534 slidably disposed within body 1520.

With particular reference to FIG. 27, handle portion 1510 is ergonomically configured to facilitate grasping of suture passer 1500, and defines a longitudinal passageway 1512 extending therethrough. Longitudinal passageway 1512 defines a minimum width suitable to slidably receive actuation shaft 1534 of plunger 1530 and includes a first chamber 1514 having a larger width than the minimum width, and a second chamber 1516 positioned distally adjacent first chamber 1514 and defining a width equal to or larger than the first expanded portion 1514 in a first dimension and a width smaller than the first expanded portion 1514 in a second dimension (the second dimension is shown in FIG. 27). As such, first and second shoulders 1515, 1517 are defined between first and second chambers 1514, 1516, and between passageway 1512 and second chamber 1516, respectively.

Elongated body 1520 is fixedly engaged to and extends distally from handle portion 1510. Elongated body 1520 defines a longitudinal lumen 1522 in communication with longitudinal passageway 1512, thus permitting actuation shaft 1534 of plunger 1530 to extend through handle portion 1510 and into elongated body 1520. Elongated body 1520 further defines an open distal tip 1524 that may be pointed or otherwise configured to facilitate penetration through tissue, and a window 1526 defined within the side wall of elongated body 1520 near the distal region thereof.

Suture 1550 includes first and second ends 1552, 1554, each having a retention member 1553, 1555 secured thereto. Retention members 1553, 1555 and, thus, first and second ends 1552, 1554 of suture 1550 are initially disposed within longitudinal lumen 1522 of elongated body 1520 adjacent window 1524. Retention members 1553, 1555 are dimensioned to enable passage through openings 1139, 1149 of arms 1130, 1140 (see FIG. 22) in only one or a few particular orientations, thus inhibiting accidental or un-intended withdrawal of retention members 1553, 1555 through openings 1139, 1149 of arms 1130, 1140 (FIG. 22).

Plunger 1530, as mentioned above, includes an actuator 1532 extending proximally from handle portion 1510 and an actuation shaft 1534 slidably disposed within body 1520. Actuation shaft 1534 includes a biasing member 1536 disposed thereabout and a selector 1538 engaged about actuation shaft 1534 proximally of biasing member 1536. Biasing member 1536 is longitudinally maintained between selector 1538 and second shoulder 1517 defined within handle potion 1510. Selector 1538 defines a rectangular or other non-radially-symmetrical configuration shaped complementary to the first and second dimensions of second chamber 1516 such that, in a first orientation of selector 1538 relative to longitudinal passageway 1512 (FIG. 27), selector 1538 is inhibited from translating from first chamber 1514 of longitudinal passageway into second chamber 1516 of longitudinal passageway 1512, and such that, in a second orientation of selector 1538 relative to longitudinal passageway 1512, selector 1538 is permitted to translate distally from first chamber 1514 into second chamber 1516. Thus, in the first orientation, plunger 1530 is translatable from a proximal position to an intermediate position, wherein selector 1538 abuts first shoulder 1515, while, in the second orientation, plunger 1530 is translatable distally from the proximal position to a distal position, wherein selector 1538 abuts second shoulder 1517. Biasing member 1536 biases plunger 1530 towards the proximal position.

Referring again to FIGS. 22, 26, and 27, in use, with plunger 1530 disposed in the proximal position (FIG. 27), elongated body 1520 of suture passer 1500 may be inserted through one of the needle lumens 1114 of shaft 1110, through tissue, and through the opening 1139 defined within the corresponding arm 1130. Thereafter, plunger 1530, in the first orientation, may be translated distally from the proximal position to the intermediate position such the distal end of actuation shaft 1534 contacts retention member 1553 which, in turn, contacts retention member 1555 and urges retention member 1555 distally through open distal tip 1524 of elongated body 1520. Alternatively, suture passer 1500 may be configured to eject retention members 1553, 1555 through window 1526. Plunger 1530 may then be withdrawn proximally from arm 1130, tissue, and shaft 1110. As noted above, the dimensions of retention member 1555 inhibit proximal translation of retention member 1555 through arm 1130, thus maintaining second end 1554 of suture 1550 in engagement with arm 1130.

Next, elongated body 1520 of suture passer 1500 may be inserted through the other needle lumen 1114 of shaft 1110, through tissue, and through the opening 1149 defined within the corresponding arm 1140. Thereafter, plunger 1530 may be transitioned to the second orientation, e.g., via rotating plunger 1530 relative to body 1520, such that plunger 1530 may be translated distally from the proximal position to the distal position. Translation of plunger 1530 to the distal position allows the distal end of actuation shaft 1534 to contact and eject the retention member 1553 through open distal tip 1524 of elongated body 1520. Plunger 1530 may then be withdrawn proximally from arm 1140, tissue, and shaft 1110, leaving retention member 1553 and first end 1553 of suture 1550 retained in engagement with arm 1140.

Ultimately, wound closure device 1200 may be returned to the retracted position and withdrawn from the opening in tissue, leaving ends 1552, 1554 of suture 1550 to be tied off in a configuration similar to that shown in FIG. 9.

Turning to FIGS. 28-29B, another suture passer 1600 configured for use with a wound closure device 1200' similar to wound closure device 1200 (FIG. 23) is shown, although suture passer 1600 may alternatively be configured for use with any other suitable wound closure device. Wound closure device 1200', as shown in FIG. 28, is similar to wound closure device 1200 (FIG. 23) but differs mainly in that wound closure device 1200' only includes a single arm 1230'. Wound closure device 1200' further differs in that second segment 1236' of arm 1230' includes a retention member dock 1237' and plunger 1220' defines a recess 1223' configured to receive retention member dock 1237' when arm 1230' is disposed in the retracted position. Suture passer 1600 and wound closure device 1200' are configured for use with a suture 1650 including a retention member 1653 disposed at an end 1652 thereof. Retention member 1653 includes one or more resilient engagement legs 1655 and defines an inner pocket 1657.

Referring to FIGS. 29A-29B, suture passer 1600 generally includes a handle portion 1610, an elongated body 1620 extending distally from handle portion 1610, and a plunger 1630. Plunger 1630 includes an actuator 1632 extending proximally from handle portion 1610 and an actuation shaft 1634 slidably disposed within body 1620.

Handle portion 1610 is ergonomically configured to facilitate grasping of suture passer 1600 and defines a longitudinal passageway (not shown) configured to receive actuation shaft 1634. Elongated body 1620 is fixedly engaged to and extends distally from handle portion 1610. Elongated body 1620 defines a longitudinal lumen 1622 in communication with the passageway (not shown) of handle portion 1610 at its proximal end and an open distal end. Elongated body 1620 further includes a distal portion 1624 defining one or more engagement recesses 1626. Distal portion 1624 is configured to releasably retain a retention member 1653 of suture 1650, as detailed below.

A biasing member (not shown) may be provided for biasing plunger 1630 towards a proximal position, wherein actuation shaft 1634 does not extend distally from elongated body 1620. Plunger 1630 is selectively translatable relative to handle portion 1610 and elongated body 1620 between this proximal position (FIG. 29A) and a distal position (FIG. 29B), wherein a portion of actuation shaft 1634 extends distally from the distal end of elongated body 1620.

With reference again to FIGS. 28-29B, in use, retention member 1653 is initially engaged about elongated body 1620 such that distal portion 1624 of elongated body 1620 is received within inner pocket 1657 of retention member 1653 and such that the one or more resilient engagement legs 1655 of retention member 1653 are engaged within the one or more engagement recesses 1626, as shown in FIG. 29A.

With retention member 1653 engaged about distal portion 1624 of elongated body 1620, elongated body 1620 of suture passer 1600 may be inserted through the needle lumen 1214' of shaft 1210' of wound closure device 1200', through tissue, and through the opening 1239' defined within first segment 1234' of arm 1230'. Elongated body 1620 is advanced through arm 1230' until retention member 1653 is received within dock 1237', e.g., via friction-fitting or other suitable releasable engagement. Thereafter, plunger 1630 may be translated to the distal position such that actuation shaft 1634 extends distally from elongated body 1620 and into contact with retention member 1653 under sufficient urging to flex resilient engagement legs 1655 outwardly and out of engagement from within engagement recesses 1626 to disengage retention member 1653 from about distal portion 1624 of elongated body 1620. Once retention member 1653 has been disengaged, suture passer 1600 may be withdrawn, leaving retention member 1653 engaged within dock 1637' and a portion of suture 1650 extending through tissue.

Wound closure device 1200' may then be rotated relative to the opening in tissue such that arm 1230' is positioned on an opposite side of the opening in tissue. Thereafter, elongated body 1620 of suture passer 1600 may be once again inserted through the needle lumen 1214' of shaft 1210' of wound closure device 1200', through tissue, and through the opening 1239' defined within first segment 1234' of arm 1230'. Elongated body 1620 is advanced through arm 1230' with sufficient urging such that distal portion 1624 of elongated body 1620 is urged into inner pocket 1657 of retention member 1653 and such that the one or more resilient engagement legs 1655 of retention member 1653 are initially flexed outwardly and then resiliently returned into engagement within engagement recesses 1626. Thus, with retention member 1653 once again engaged to suture passer 1600, suture passer 1600 may be withdrawn to pull retention member 1653 and a portion of suture 1650 proximally through tissue on the other side of the opening, ultimately allowing suture 1650 to be tied off in a configuration similar to that shown in FIG. 9.

As an alternative to defining engagement recesses 1626, or in addition thereto, distal portion 1624 of elongated body 1620 of suture passer 1600 may define a plurality of proximally-extending fingers (not shown). In such a configuration, the proximally-extending fingers are flexed inwardly to permit passage of distal portion 1624 of elongated body 1620 into the interior of the retention member, e.g., retention member 1653. However, once disposed therein, withdrawal of distal portion 1624 of elongated body 1620 is inhibited via engagement of the proximally-extending fingers with the interior surface of the retention member. Other suitable configurations are also contemplated.

Referring to FIGS. 30-32, another wound closure device provided in accordance with the present disclosure is shown generally as wound closure device 1200". Wound closure device 1200" is configured for use with a suture grasper 1270 (FIG. 32) and a suture 1290, although any of these components may alternatively or additionally be used in accordance with any of the other components detailed herein.

Suture 1290 defines first and second ends 1292 and an intermediate portion 1294. A retention member 1295 releasably mounted on a cartridge 1298 is defined at each end 1292 of suture 1290. Retention members 1295 are formed via weaving, knitting, meshing, stitching, or otherwise intertwining the end 1292 of suture 1290 (alone or with other materials) to define a suture web 1296 defining a plurality of openings 1297. Retention members 1295 may be releasably retained on cartridge 1298 in any suitable fashion, e.g., via adhesives, releasable clips, etc.

Cartridges 1298 each includes a base 1299a and legs 1299b engaged to base 1299a on either end thereof. Legs 1299b are configured for releasable receipt within engagement slots 1284 defined within second segments 1282 of arms 1280 of wound closure device 1200", as will be detailed below. Bases 1299a are configured to retain retention members 1295 thereon, e.g., via adhesives, releasable clips, etc., and further define openings 1299c within the retention-member supporting surface thereof, the importance of which will be detailed below.

Wound closure device 1200" is similar to wound closure device 1200 (FIG. 23) and further includes a slot 1284 defined within the second segment 1282 of each arm 1280. Each slot 1284 is configured to releasably receive a retention member 1295 retaining an end 1292 of a suture 1290. More specifically, slots 1284 are shaped complementary to legs 1299b, e.g., defining "T"-shaped configurations, such that legs 1299b may be engaged with slots 1284 via transversely sliding cartridges 1298 relative to arms 1280, as shown in FIG. 31. In preparation for use, with wound closure device 1200 disposed in the deployed configuration (FIG. 30), cartridges 1298 may be engaged within arms 1280 as noted above and such that intermediate portion 1294 of suture extends about the distal end of wound closure device 1200". Thereafter, wound closure device 1200" may be moved to the retracted condition to facilitate insertion through the opening in tissue.

Continuing with reference to FIGS. 30-32, in use, once wound closure device 1200" has been inserted through the opening in tissue and transitioned to the deployed condition, suture grasper 1270, lead by hooked distal end 1272 may be inserted through wound closure device 1200", tissue, and into one of the arms 1280. More specifically, hooked distal end 1272 of suture grasper 1270 is urged into one of the arms 1280 and through one of openings 1297 in web 1296 of retention member 1295 and opening 1299c in base 1299a of cartridge 1298. Once inserted to this position, suture grasper 1270 may be retracted such that the hooked distal end 1272 hooks or grasps at least a portion of the retention member 1295 of suture 1290, disengages the retention member 1295 from cartridge 1298 and retracts the retention member 1295 of suture 1290 proximally through tissue. The process may then be repeated with respect to the other arm member 1280, ultimately allowing suture 1290 to be tied off in a configuration similar to that shown in FIG. 9. For subsequent use, the spent cartridges 1298 are removed from arms 1280 and wound closure device 1200" is loaded with a new suture 1290, similarly as detailed above.

Figure 33:
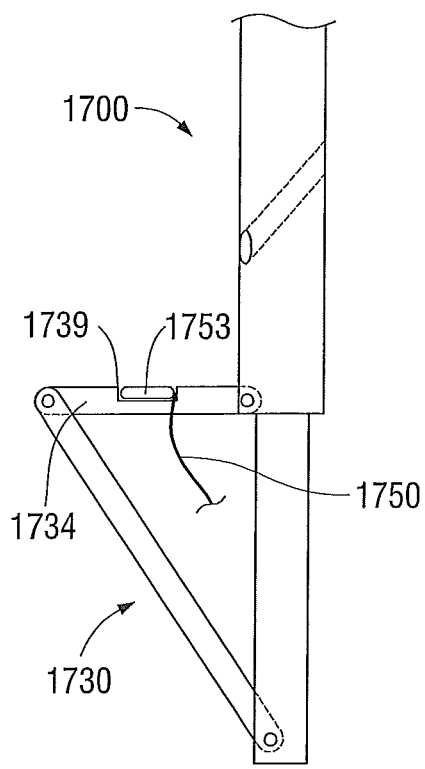
FIG. 33 is a side view of a distal portion of another wound closure device provided in accordance with the present disclosure retaining a portion of a suture thereon.

With reference to FIG. 33, another wound closure device 1700 similar to wound closure device 1200' (FIG. 28) is shown. Wound closure device 1700 differs from wound closure device 1200' (FIG. 28) mainly in that, rather than providing a retention dock, opening 1739 located on first segment 1734 of arm 1730 is configured to releasably retain a retention member 1753 disposed at an end of a suture 1750, thus allowing the retention member 1753 and, thus, the end of suture 1750 to be retrieved via a suitable suture grasper and withdrawn proximally through tissue, similarly as detailed above with respect to previous embodiments. Various embodiments of retention members and corresponding suture graspers suitable for this purpose are detailed below with reference to FIGS. 34-36.

Figure 34:
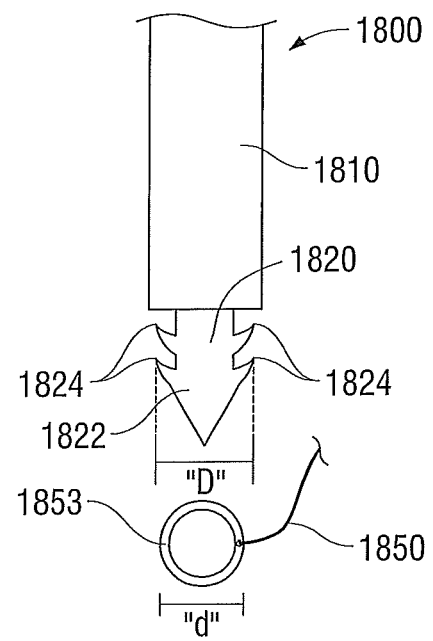
FIG. 34 illustrates a suture member and distal portion of a corresponding suture grasper provided in accordance with the present disclosure.

Referring to FIG. 34, a suture grasper 1800 and corresponding retention member 1853 configured for use therewith are shown. Retention member 1853 defines a flexible ring, e.g., formed from an elastomeric material, having an initial at-rest diameter "d." Retention member 1853 may further defines an aperture through the outer portion thereof that is configured to receive an end of a suture 1850, although suture 1850 may alternatively be looped about retention member 1853, e.g., through the central opening thereof. Retention member 1853 is configured for releasable receipt within opening 1739 of arm 1730 (FIG. 33).

Suture grasper 1800 includes an outer shaft 1810 and a needle 1820 extending distally from outer shaft 1810. Needle 1820 defines a conical distal end 1822 configured to facilitate penetration through tissue, although other configurations are also contemplated. Needle 1820 further defines one or more pairs of opposed barbs 1824. Each pair of barbs 1824 is spaced-apart and curved or angled proximally. The maximum diameter "D" of needle 1820, as defined by the free ends of each pair of barbs 1824, is larger than the diameter "d" of retention member 1853. Thus, upon insertion of needle 1820 into opening 1739 of arm 1730 (FIG. 33), retention member 1853 is flexed outwardly to permit passage of distal end 1822 of needle 1820 therethrough. Once distal end 1822 of needle 1820 has passed through retention member 1853, the proximally-facing barbs 1824 inhibit disengagement of retention member 1853 from about distal end 1822 of needle 1820. Accordingly, needle 1820 and the end of suture 1850 may together be withdrawn through tissue.

Figure 35:
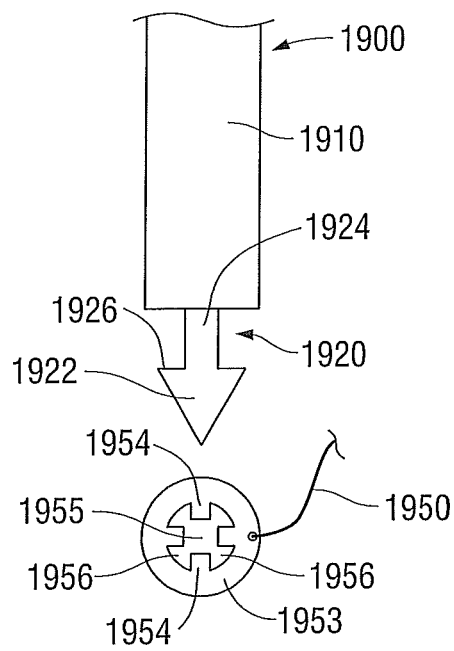
FIG. 35 illustrates another suture member and distal portion of a corresponding suture grasper provided in accordance with the present disclosure.

FIG. 35 shows another suture grasper 1900 and corresponding retention member 1953 configured for use therewith. Suture grasper 1900 and retention member 1953 are similar to suture grasper 1800 and retention member 1853 (FIG. 34), respectively. Retention member 1953 differs from retention member 1853 (FIG. 34) mainly in that the retention member 1953 defines a flexible ring having an irregular central opening 1955. More specifically, portions 1954 of retention member 1953 protrude inwardly into central opening 1955 to reduce central opening 1955 at various positions and/or cut-outs 1956 are defined within retention member 1953 to enlarge central opening 1955 at various positions.

Suture grasper 1900, similar to suture grasper 1800 (FIG. 34) includes an outer shaft 1910 and a needle 1920 extending distally from outer shaft 1910. Needle 1920 defines a conical distal end 1922 configured to facilitate penetration through tissue, although other configurations are also contemplated. Conical distal end 1922 of needle 1920 and body 1924 of needle 1920 cooperate to define a proximally-facing shoulder 1926. Similar to barbs 1824 of suture grasper 1800 (FIG. 34), conical distal end 1922 permits insertion of needle 1920 through retention member 1953, while shoulder 1926 and the irregular central opening 1955 of retention member 1953 cooperate to inhibit withdrawal of needle 1920 from retention member 1953. Accordingly, once engaged, needle 1920 and the end of suture 1950 may together be withdrawn through tissue.

Figure 36:
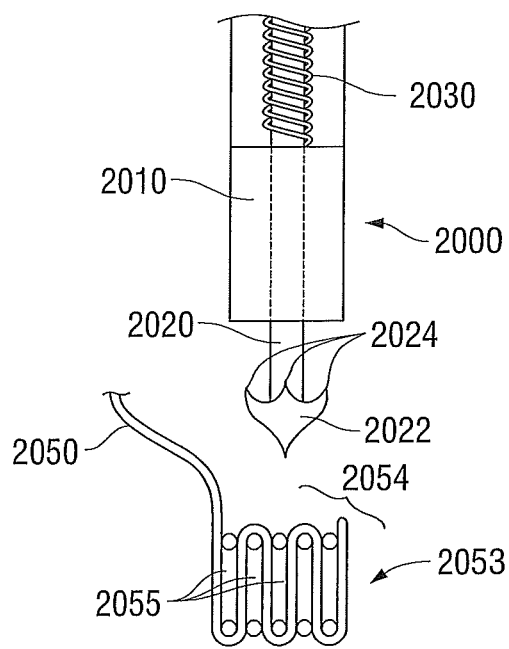
FIG. 36 illustrates another suture member and distal portion of a corresponding suture grasper provided in accordance with the present disclosure.

Turning to FIG. 36, another suture grasper 2000 and corresponding retention member 2053 configured for use therewith are shown. Retention member 2053 is formed via weaving, knitting, meshing, stitching, or otherwise intertwining the end of suture 2050 (alone or with other materials) to define a suture web 2054 defining a plurality of openings 2055.

Suture grasper 2000 is similar to suture grasper 1800 (FIG. 34) but differs mainly in that conical distal tip 2022 of needle 2020 of suture grasper 2000 includes a plurality of radially-spaced barbs 2024 disposed thereabout. Suture grasper 2000 further differs in that needle 2020 is slidable relative to outer shaft 2010 and is biased proximally relative to outer shaft 2010 via a biasing member 2030. In the proximal position (not shown), distal tip 2022 of needle 2020 is at least partially disposed within outer shaft 2010.

In use, needle 2020 is moved to a distal position (FIG. 36) against the bias of biasing member 2030 such that conical distal end 2022 of needle 2020 extends distally from outer shaft 2010. Thereafter, needle 2020 is urged distally relative to retention member 2053 such that conical distal end 2022 of needle 2020 is urged into contact with suture web 2054 under sufficient urging to enlarge and pass distally through one of the web openings 2055 defined by the portions of suture forming suture web 2054. Conical distal end 2022 of needle 2020 facilitates this distal passing through one of the web openings 2055. However, once barbs 2024 have been advanced distally through the web opening 2055 to a position distal of suture web 2054, radially-spaced barbs 2024 inhibit proximal withdrawal of needle 2020 from web opening 2055. Rather, upon proximal translation of needle 202 relative to suture web 2054, barbs 2024 are engaged with the portions of suture forming suture web 2054. As such, when needle 2020 is moved back to the proximal position, e.g., under bias, retention member 2053 is likewise retracted proximally into outer shaft 2010 such that needle 2020 and the end of suture 2050 may together be withdrawn through tissue.

With reference to FIGS. 37-41, another wound closure device 2100 provided in accordance with the present disclosure is shown generally as wound closure device 2100. Wound closure device 2100 is configured for use with a sleeve 2200 and a suture grasper 2300, as will be detailed below.

Figure 38:
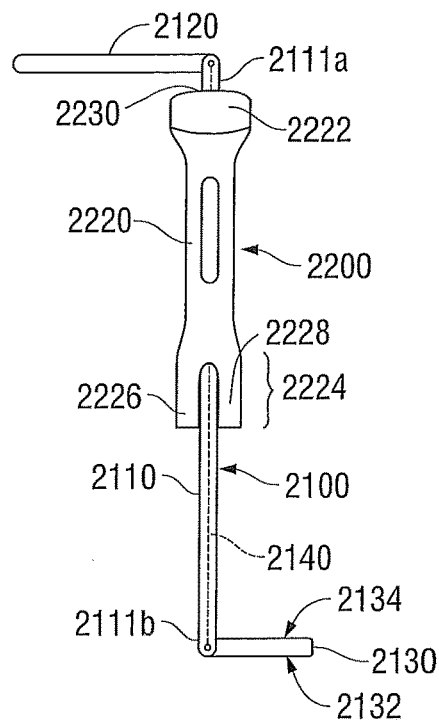
FIG. 38 is a side view of the wound closure device of FIG. 37, disposed in an articulated condition.
Figure 39:
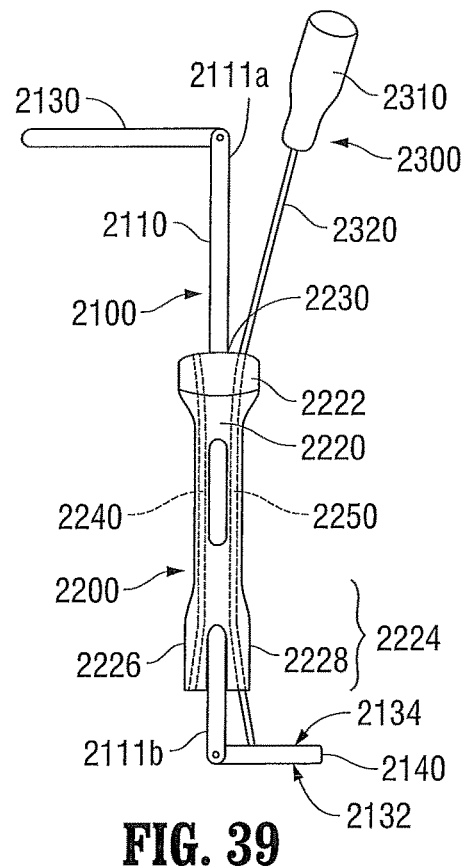
FIG. 39 is a side view of the wound closure device of FIG. 37, disposed in the articulated condition and including a suture grasper inserted therethrough.
Figure 41:
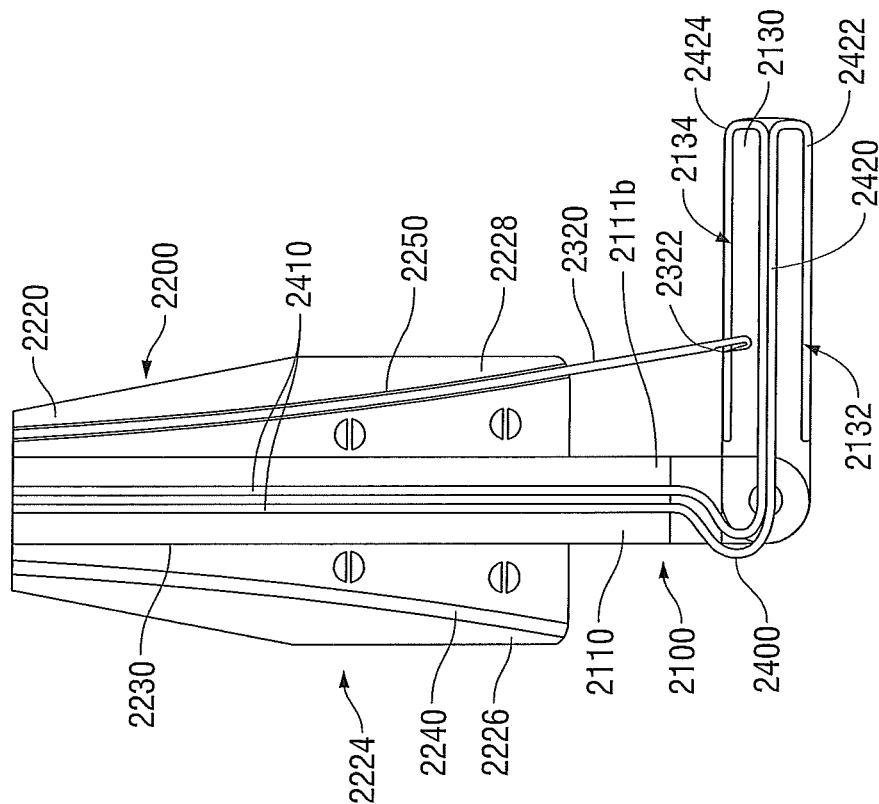
FIG. 41 is an enlarged, longitudinal cross-sectional view of a distal end of the wound closure device of FIG. 37, disposed in the articulated condition and including the suture grasper of FIG. 40 inserted therethrough.

Wound closure device 2100 includes an elongated shaft 2110, a proximal arm 2120 pivotably coupled to elongated shaft 2110 at the proximal end 2111a of elongated shaft 2110, and a distal arm 2130 pivotably coupled to elongated shaft 2110 at the distal end 2111b of elongated shaft 2110. Proximal and distal arms 2120, 2130 are coupled to one another via one or more linkages 2140, e.g., cables, such that pivoting of proximal arm 2120 relative to elongated shaft 2110 in a first direction effects corresponding pivoting of distal arm 2130 relative to elongated shaft 2110 in an opposite direction (see FIGS. 38 and 39). Proximal arm 2120 remains external of tissue during use, thus functioning as an actuator that enables the user to selectively pivot distal arm 2130, which is internally-disposed, to a desired position. Distal arm 2130 includes first and second opposed surfaces 2132, 2134, respectively. As can be appreciated, depending on the direction of pivoting of distal arm 2130, first surface 2132 may be proximally-facing (as shown in FIGS. 38, 39, and 41), or second surface 2134 may be proximally-facing (when distal arm 2130 is pivoted in the opposite direction). Elongated shaft 2110 is configured for insertion through the opening in tissue.

With particular reference to FIG. 41, wound closure device 2100 is further configured to retain a suture 2400 therein. More specifically, suture 2400 includes an body portion 2410 that is routed through elongated shaft 2110, and end portions 2420 having first and second segments 2422, 2424 operably disposed about first and second surfaces 2132, 2134, respectively, of distal arm 2130, and releasably retained thereon in any suitable manner, e.g., via adhesives, tacking, etc.

Referring again to FIGS. 37-41, sleeve 2200 is similar to sleeve 320 of needle and sleeve assembly 300 (FIG. 4) and generally includes a body 2220 having a proximal collar 2222 and a bifurcated distal end 2224 defining first and second fingers 2226, 2228. A central passageway 2230 is configured to slidably receive shaft 2110 of wound closure device 2100 and extends longitudinally through body 2220 of sleeve 2100. First and second curved needle lumens 2240, 2250 are defined through body 2220 on either side of central passageway 2230. The curvature of needle lumens 2240, 2250 directs a needle inserted therethrough towards the portion of suture to be retrieved, as will be detailed below.

Figure 40:
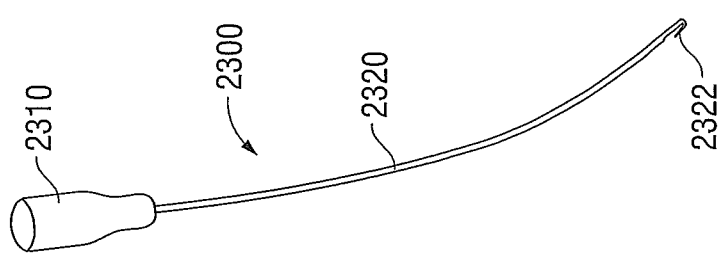
FIG. 40 is a side, perspective view of the suture grasper illustrated in FIG. 39.

With reference to FIG. 40, suture grasper 2300 includes a handle portion 2310 and a needle 2320 extending distally from handle portion 2310. Needle 2320 defines a pre-curved configuration having a radius of curvature similar to that of needle lumens 2240, 2250 of sleeve 2200 (FIG. 41) and/or defines a flexible configuration to facilitate insertion of needle 2320 through either needle lumen 2240, 2250 (FIG. 41). Needle 2320 further includes a hooked or "J"-shaped distal end 2322.

With continued reference to FIGS. 37-41, the use and operation of wound closure device 2100 is similar to that of wound closure device 100 (FIG. 1) with respect to use in conjunction with an access device, e.g., surgical access device 200 (FIG. 3), and sleeve 2200. More specifically, referring initially to FIG. 37, once wound closure device 2100 has been inserted through the opening in tissue in a linear position (and the access device removed), sleeve 2200 may be slid distally over proximal arm 2120 such that sleeve 2200 is disposed about elongated shaft 2110. Thereafter, as shown in FIG. 38, proximal arm 2120 may be pivoted relative to elongated shaft 2110 to pivot distal arm 2130 such that second surface 2134 of distal arm 2130 and second segment 2424 of suture 2400 (FIG. 41) are positioned proximally-adjacent and facing an internal surface of tissue. Sleeve 2200 may subsequently be approximated relative to tissue to grasp or retain tissue between finger 2228 of sleeve 2200 and distal arm 2130 of wound closure device 2100.

Referring to FIGS. 39 and 41, once the above-noted position has been achieved, needle 2320 of suture grasper 2300, lead by hooked distal end 2322 of needle 2320, is inserted through curved needle lumen 2250 and through tissue such that hooked distal end 2322 of needle 2320 is directed towards second surface 2134 of distal arm 2130. Suture grasper 2300 may then be manipulated to hook second segment 2424 of suture 2400 and withdrawn proximally to pull second segment 2424 proximally through tissue. Thereafter, proximal arm 2120 may be pivoted relative to elongated shaft 2120 in the opposite direction to pivot distal arm 2130 such that first surface 2132 of distal arm 2130 and first segment 2422 of suture 2400 (FIG. 41) are positioned proximally-adjacent and facing an internal surface of tissue, on the opposite side of the opening in tissue. Needle 2320 may then be inserted through curved needle lumen 2240 and through tissue to retrieve and withdrawn first segment 2422 of suture 2400 proximally through tissue, ultimately such that suture 2400 may be tied off in a configuration similar to that shown in FIG. 9.

Figure 37:
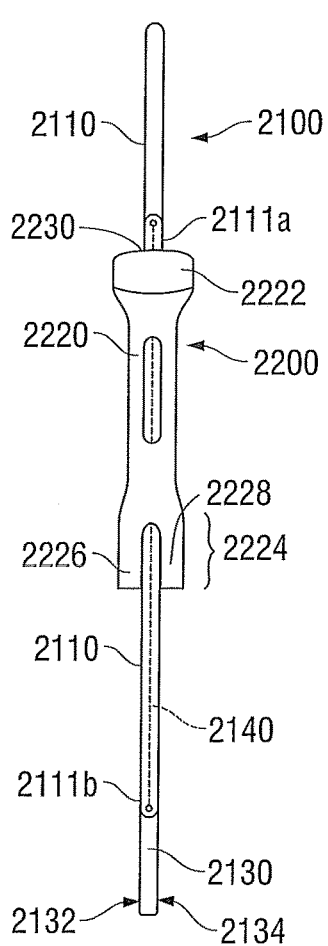
FIG. 37 is a side view of another wound closure device provided in accordance with the present disclosure, disposed in a linear condition.

With reference to FIGS. 42-43B, another wound closure device 2500 provided in accordance with the present disclosure is shown generally as wound closure device 2500. Wound closure device 2500 is configured for use with sleeve 2200 and suture grasper 2300, similarly as detailed above with respect to wound closure device 2100 (FIGS. 37-39). Accordingly, only the differences between wound closure device 2500 and wound closure device 2100 (FIGS. 37-39) are detailed below.

Wound closure device 2500 includes an outer shaft 2510, and a plunger 2520 slidably disposed within outer shaft 2510. Plunger 2520 includes first and second spring arms 2530, 2540 extending from the distal end thereof. Spring arms 2530, 2540 are biased towards an outwardly-extending position, wherein spring arms 2530, 2540 extend radially outwardly from plunger 2520 in opposite directions relative to one another, as shown in FIG. 43B. Plunger 2520 is slidable relative to outer shaft 2510 between a retracted condition (FIG. 43A), wherein spring arms 2530, 2540 are disposed within outer shaft 2510 in close proximity to one another, and a deployed condition (FIG. 43B), wherein spring arms 2530, 2540 extend distally from outer shaft 2510, thus allowing spring arms 2530, 2540 to achieve the outwardly-extending position.

A suture 2600 configured for use with wound closure device 2500 includes an body 2610 routed through outer shaft 2510, a first end 2620 releasably looped about the free end of first spring arm 2530, and a second end 2630 releasably looped about the free end of second spring arm 2540. Thus, with plunger 2520 disposed in the deployed position, suture grasper 2300 may be utilized to sequentially retrieve first and second ends 2620, 2630 of suture, such that suture 2600 may ultimately be tied off in a configuration similar to that shown in FIG. 9.

Turning to FIGS. 44A and 44B, as an alternative to releasably looping first and second ends 2620, 2630 of suture 2600 about the free ends of spring arms 2530, 2540 (FIG. 43B), respectively, another embodiment of spring arms 2550 (only one of which is shown) may be provided, similar to spring arms 2530, 2540 (FIG. 43B). Each spring arm 2550 includes bifurcated distal end 2552 having first and second spaced-apart fingers 2554, 2556 and defining an opening 2558 between fingers 2554, 2556. At least one of fingers 2554, 2556 includes a protrusion 2559 disposed at the free end thereof to substantially enclose opening 2558, as shown in FIG. 44A. Each spring arm 2550 is configured to receive a knotted end 2710 of a suture 2700 with the knot 2720 disposed one side of opening 2558 and the suture 2700 extending through the opening 2558, as shown in FIG. 44B. Ends 2710 of suture 2700 may be installed on spring arms 2550 via urging suture 2700 between fingers 2554, 2556 from the free ends thereof sufficiently so as to permit entry of ends 2710 of suture 2700 into openings 2558. In use, upon retrieval of ends 2710 of suture 2700, ends 2710 are translated proximally with sufficient urging such that knot 2720 displaces fingers 2554, 2556, allowing knot 2720 to move through opening 2558, thereby disengaging the end 2710 of suture 2700 from its respective spring arm 2550.

Figure 45A:
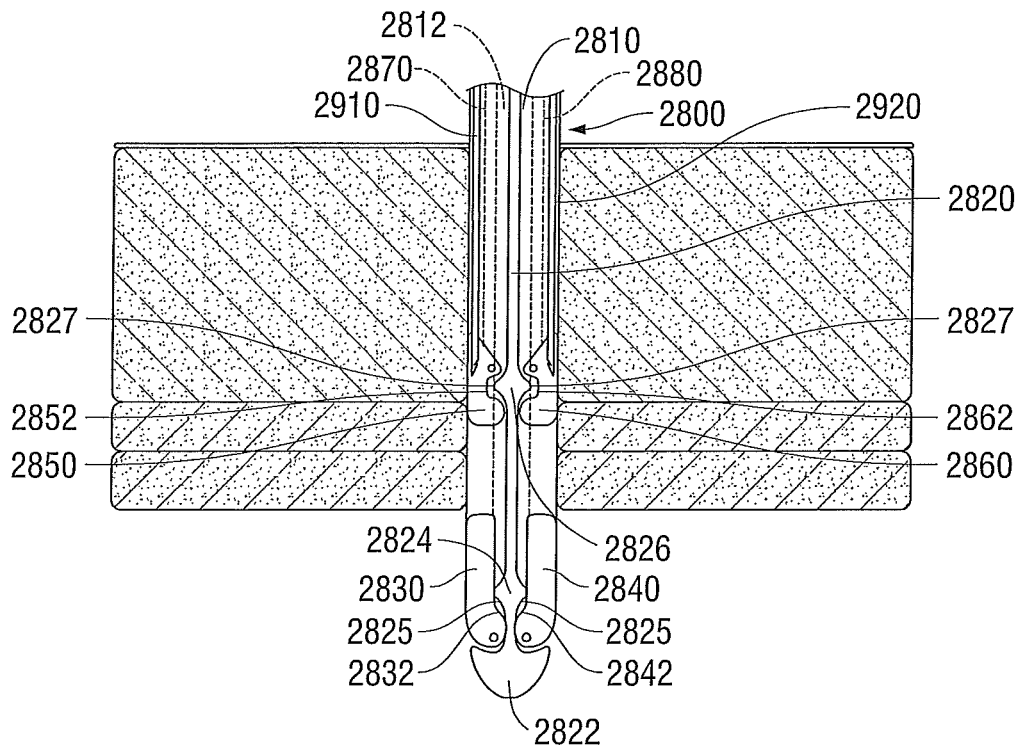
FIG. 45A is a longitudinal cross-sectional view of another wound closure device provided in accordance with the present disclosure, positioned within an opening in tissue and disposed in a retracted condition.
Figure 45B:
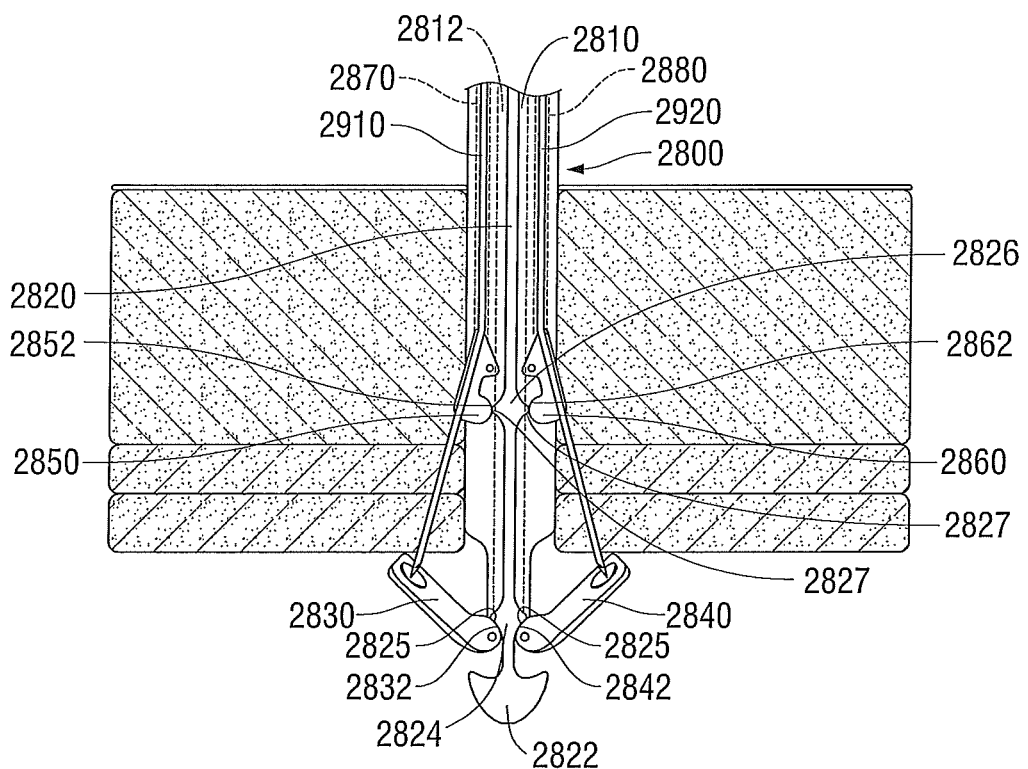
FIG. 45B is a longitudinal cross-sectional view of the wound closure device of FIG. 45A, positioned within an opening in tissue and disposed in a deployed condition.

Referring to FIGS. 45A-45B, another wound closure device 2800 provided in accordance with the present disclosure is shown generally as wound closure device 2800. Wound closure device 2800 includes an elongated shaft 2810 and a plunger 2820 slidably received within shaft 2810. A pair of selectively deployable arms 2830, 2840 is operably coupled to shaft 2810 and plunger 2820 and a pair of selectively deployable needle guides 2850, 2860 is operably coupled to shaft 2810. Wound closure device 2800 further includes a needle assembly having first and second flexible needles 2910, 2920, respectively, which may be engaged to plunger 2820 for movement therewith, similar to wound closure device 500 (FIGS. 11A-11B), or may be manually advancable/retractable, similar to needle assembly 310 (FIG. 4).

Shaft 2810 is configured for insertion through a wound or other opening in tissue and defines a longitudinal bore 2812 extending therethrough that is configured to slidably receive plunger 2820. First and second arms 2830, 2840 are pivotably coupled to shaft 2810 at the distal region thereof. First and second needle guides 2850, 2860 are pivotably coupled to shaft 2810 near the distal region thereof but longitudinally-spaced from arms 2830, 2840, proximally thereof. Arms 2830, 2840 and guides 2850, 2860 are selectively pivotable relative to shaft 2810 and in concert with one another between a retracted position (FIG. 45A) and a deployed position (FIG. 45B). In the retracted position (FIG. 45A), arms 2830, 2840 and guides 2850, 2860 are disposed within the outer dimensions of shaft 2810 to define a low-profile configuration that facilitates insertion and removal of wound closure device 2800. In the deployed position (FIG. 45B), arms 2830, 2840 and guides 2850, 2860 extend outwardly from shaft 2810. Shaft 2810 further defines first and second needle lumens 2870, 2880 disposed on either side of longitudinal bore 2812.

Plunger 2820 is slidably received within longitudinal bore 2812 of shaft 2810 and includes a distal end cap 2822 disposed at the distal end of plunger 2820, a first cam block 2824 proximally-spaced from distal end cap 2822, and a second cam block 2826 proximally-spaced from first cam block 2824. First cam block 2824 includes a pair of opposed cam surfaces 2825 configured to contact cam surfaces 2832, 2842 of arms 2830, 2840, respectively, to pivot arms 2830, 2840 between the retracted and deployed positions upon translation of plunger 2820 through shaft 2810. Similarly, second cam block 2826 includes a pair of opposed cam surfaces 2827 configured to contact cam surfaces 2852, 2862 of guides 2850, 2860, respectively, to pivot guides 2850, 2860 in concert with arms 2830, 2840 between the retracted and deployed positions upon translation of plunger 2820 through shaft 2810. Alternatively, as opposed to cam surfaces, plunger 2820 may be coupled to arms 2830, 2840 and guides 2850, 2860 via a rack and pinion engagement, similarly as detailed above with respect to wound closure device 100 (FIGS. 2A-2B).

Plunger 2820 is selectively translatable through and relative to shaft 2810, as a result of the above-configuration, between a proximal position (FIG. 45A), corresponding to the retracted position of arms 2830, 2840 and guides 2850, 2860, and a distal position (FIG. 45B), corresponding to the deployed position of arms 2830, 2840 and guides 2850, 2860. As shown in FIG. 45B, in the deployed position, guides 2850, 2860 are directed towards arms 2830, 2840.

Needle lumens 2870, 2880 extend longitudinally through shaft 2810 and are disposed in communication with guides 2850, 2860. Flexible needles 2910, 2920 are configured for insertion through needle lumens 2870, 2880 and into respective guides 2850, 2860 which (when disposed in the deployed position), direct flexible needle 2910, 2920, upon further distal translation thereof, through tissue and towards arms 2830, 2840. Needles 2910, 2920 may be configured to deposit and/or retrieve a portion of suture to/from arms 2830, 2840 in any suitable manner, such as those detailed above. Further, a suture (not shown) may be routed through wound closure device 2800 and/or arms 2830, 2840 for use therewith in any suitable manner, such as those detailed above.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A wound closure system, comprising:
a wound closure device configured for insertion into an opening in tissue, the wound closure device including an elongated shaft and at least one arm coupled to the shaft in a distal region of the shaft, the at least one arm movable relative to the shaft between a retracted position and a deployed position, wherein the at least one arm extends outwardly from the shaft when in the deployed position;
a sleeve defining a proximal end portion, a distal end portion, a central passage extending longitudinally through the sleeve, and at least one needle lumen extending longitudinally through the sleeve, the sleeve being removably positionable about the shaft of the wound closure device through reception of a proximal region of the shaft within the central passage such that the sleeve is slidable distally about the shaft to retain tissue between the distal end portion of the sleeve and the at least one arm when the at least one arm is in the deployed position; and
a needle assembly including a base member and at least one needle extending distally from the base member, the at least one needle slidably insertable through the at least one needle lumen of the sleeve, the base member defining a central aperture configured to receive the shaft of the wound closure device for removably positioning the base member about the shaft, the base member being slidable about the shaft and relative to the sleeve between a proximal position, wherein the at least one needle is disposed within the at least one needle lumen, and a distal position, wherein the at least one needle extends from the at least one needle lumen towards the at least one arm.

2. The wound closure system according to claim 1, wherein the wound closure device further includes a plunger slidably disposed within a central bore of the shaft, the plunger coupled to the at least one arm in a distal region of the plunger and selectively translatable relative to the shaft between a first position and a second position for moving the at least one arm between the retracted position and the deployed position.

3. The wound closure system according to claim 2, wherein the at least one arm is pivotably coupled to the shaft and has a pinion member, and wherein the plunger has at least one gear rack, the at least one gear rack disposed in meshed engagement with the pinion member such that translation of the plunger relative to the shaft pivots the at least one arm between the retracted position and the deployed position.

4. The wound closure system according to claim 2, wherein the at least one arm is pivotably coupled to the shaft and defines a first cam surface, wherein the plunger defines a second cam surface, and wherein translation of the plunger relative to the shaft urges the second cam surface into contact with the first cam surface to transition the at least one arm from the retracted position to the deployed position.

5. The wound closure system according to claim 4, wherein the at least one arm is biased towards the retracted position.

6. The wound closure system according to claim 1, wherein the at least one arm defines a suture-retaining void and wherein, in the distal position, the at least one needle extends from the at least one needle lumen into the suture-retaining void of the at least one arm.

7. The wound closure system according to claim 1, wherein the sleeve includes at least one finger, the at least one finger angled towards the at least one arm when the at least one arm is in the deployed position, the at least one needle lumen extending through the at least one finger.

8. The wound closure system according to claim 1, wherein the shaft includes a plurality of first ratchet components disposed on an outer surface of the shaft and wherein the sleeve includes at least one second ratchet component extending into the central passage, the first and second ratchet components engagable with one another to retain the sleeve in position relative to the shaft.

9. The wound closure system according to claim 1, further including a surgical access device configured for positioning within an opening in tissue, wherein the shaft is distally insertable through the surgical access device, and wherein the surgical access device is proximally movable about the shaft.

10. The wound closure system according to claim 1, further including a suture with a first portion extending distally from the shaft, a second portion extending from the first portion distally through the shaft, and a third portion extending from the second portion to the at least one arm, the third portion releasably retained via the at least one arm.

11. The wound closure system according to claim 10, wherein a distal end portion of the at least one needle is configured to retrieve the third portion of the suture when the at least one needle is in the distal position.

12. A wound closure system, comprising:
a wound closure device configured for insertion into an opening in tissue, the wound closure device including:
an elongated shaft defining a longitudinal passageway extending therethrough; and
a plunger slidably disposed within the shaft, the plunger defining a pair of spring arms extending distally therefrom, each spring arm configured to retain a portion of a suture, the spring arms biased towards a spread position wherein the spring arms extend radially outwardly from the plunger and relative to one another, the plunger slidable relative to the shaft between a retracted position, wherein the spring arms are disposed within the longitudinal passageway in a contracted position, and an extended position, wherein the spring arms extend from the shaft in the spread position;
a sleeve defining a proximal end portion, a distal end portion, a central passage extending longitudinally through the sleeve, and at least one curved needle lumen extending longitudinally through the sleeve, the sleeve being removably positionable about the shaft of the wound closure device through reception of a proximal region of the shaft within the central passage such that the sleeve is slidable distally about the shaft to retain tissue between the distal end portion of the sleeve and the spring arms when the spring arms are disposed in the spread position; and
a needle assembly including a base member and at least one needle extending distally from the base member, the at least one needle slidably insertable through the at least one curved needle lumen of the sleeve, the at least one curved needle lumen directing the at least one needle towards one of the spring arms for retrieving the portion of suture therefrom.

13. The wound closure system according to claim 12, wherein each spring arm defines a pair of fingers at a free end portion thereof, the fingers defining an opening therebetween configured to receive the portion of suture therethrough.

14. The wound closure system according to claim 12, wherein the at least one needle defines a hooked distal end.

* * * * *